(12) United States Patent
Sherts et al.

(10) Patent No.: US 8,876,736 B2
(45) Date of Patent: Nov. 4, 2014

(54) CERVICAL SIZING DEVICES AND RELATED KITS AND METHODS

(71) Applicant: CooperSurgical, Inc., Trumbull, CT (US)

(72) Inventors: Charles Sherts, Westport, CT (US); Kerry Blair, Overland Park, KS (US); Peter K. Arneson, Cheshire, CT (US); Robert Williams, Norwalk, CT (US)

(73) Assignee: CooperSurgical, Inc., Trumbull, CT (US)

( * ) Notice: Subject to any disclaimer, the term of this patent is extended or adjusted under 35 U.S.C. 154(b) by 9 days.

(21) Appl. No.: 13/860,200

(22) Filed: Apr. 10, 2013

(65) Prior Publication Data

US 2013/0231589 A1    Sep. 5, 2013

Related U.S. Application Data

(63) Continuation of application No. 12/916,990, filed on Nov. 1, 2010, now Pat. No. 8,439,850.

(51) Int. Cl.
*A61B 5/107* (2006.01)
*A61B 5/00* (2006.01)

(52) U.S. Cl.
CPC ............. *A61B 5/1076* (2013.01); *A61B 5/4331* (2013.01); *A61B 5/6847* (2013.01)
USPC ............................................ 600/591; 33/512

(58) Field of Classification Search
CPC ...... A61B 5/107; A61B 5/435; A61B 5/4331; A61B 5/1076

USPC .............................................. 600/591; 33/512
See application file for complete search history.

(56) References Cited

U.S. PATENT DOCUMENTS

| 1,269,027 | A | * | 6/1918 | White | 33/807 |
| 1,856,295 | A | | 5/1932 | Sovatkin | |
| 2,186,143 | A | | 1/1940 | Neugass | |
| 2,456,806 | A | * | 12/1948 | Wolffe | 33/512 |
| 2,744,708 | A | | 5/1956 | Bedford, Jr. | |
| 3,096,764 | A | | 7/1963 | Hiebert | |

(Continued)

FOREIGN PATENT DOCUMENTS

| DE | 20110921 | 12/2001 |
| DE | 69532474 | 11/2004 |

(Continued)

OTHER PUBLICATIONS

"KOH Cup Vaginal Fornices Delineator & Colpo-Pneumo Occluder," *The Koh Colpotomizer™ System*, Directions for Use; 6 pages; Sep. 2008.

(Continued)

*Primary Examiner* — Sean Dougherty
*Assistant Examiner* — Michael C Stout
(74) *Attorney, Agent, or Firm* — Fish & Richardson P.C.

(57) ABSTRACT

This disclosure relates to cervical sizing devices and related kits and methods. In some aspects, a cervical sizing device includes an elongate arm and a member positioned at a distal end region of the elongate arm. The cervical sizing device can be used to determine an approximate size of a cervix when the member is brought into contact with an outer surface of the cervix.

14 Claims, 13 Drawing Sheets

(56) References Cited

U.S. PATENT DOCUMENTS

| | | | | |
|---|---|---|---|---|
| 3,131,690 | A | 5/1964 | Innis et al. | |
| 3,153,267 | A | 10/1964 | Rowland, Jr. | |
| 3,196,865 | A | 7/1965 | Rose | |
| 3,749,088 | A | 7/1973 | Kohlmann | |
| 3,766,909 | A | 10/1973 | Ozbey | |
| 3,768,459 | A | 10/1973 | Cannon et al. | |
| 3,769,983 | A | 11/1973 | Merav | |
| 3,877,433 | A | 4/1975 | Librach | |
| 3,878,848 | A | 4/1975 | Hiebert | |
| 3,898,738 | A * | 8/1975 | Linder | 433/159 |
| 3,948,270 | A | 4/1976 | Hasson | |
| 4,022,208 | A | 5/1977 | Valtchev | |
| 4,066,071 | A | 1/1978 | Nagel | |
| 4,141,345 | A * | 2/1979 | Allen et al. | 600/591 |
| 4,207,902 | A * | 6/1980 | Krementsov | 600/591 |
| 4,226,025 | A * | 10/1980 | Wheeler | 33/512 |
| D261,302 | S * | 10/1981 | Wheeler | D24/140 |
| 4,323,057 | A | 4/1982 | Jamieson | |
| 4,430,076 | A | 2/1984 | Harris | |
| 4,476,871 | A | 10/1984 | Hon | |
| 4,533,349 | A | 8/1985 | Bark | |
| 4,562,832 | A | 1/1986 | Wilder et al. | |
| 4,597,030 | A | 6/1986 | Brody et al. | |
| 4,611,603 | A * | 9/1986 | Kelso et al. | 600/588 |
| 4,627,421 | A | 12/1986 | Symbas et al. | |
| 4,682,609 | A * | 7/1987 | Parsons | 600/588 |
| 4,719,925 | A * | 1/1988 | Parsons | 600/588 |
| 4,775,362 | A | 10/1988 | Kronner | |
| 4,807,625 | A | 2/1989 | Singleton | |
| 4,823,167 | A | 4/1989 | Manska et al. | |
| 4,981,355 | A | 1/1991 | Higgins | |
| 4,996,974 | A | 3/1991 | Ciarlei | |
| 4,997,419 | A | 3/1991 | Lakatos et al. | |
| D321,055 | S * | 10/1991 | Carchidi | D24/152 |
| 5,059,198 | A | 10/1991 | Gimpelson | |
| 5,104,377 | A | 4/1992 | Levine | |
| 5,174,276 | A | 12/1992 | Crockard | |
| 5,181,842 | A | 1/1993 | Sunderland et al. | |
| 5,209,754 | A | 5/1993 | Ahluwalia | |
| 5,232,443 | A | 8/1993 | Leach | |
| 5,237,985 | A | 8/1993 | Hodgson et al. | |
| 5,242,240 | A | 9/1993 | Gorham | |
| 5,259,836 | A | 11/1993 | Thurmond et al. | |
| 5,273,026 | A | 12/1993 | Wilk | |
| 5,338,297 | A | 8/1994 | Kocur et al. | |
| 5,353,784 | A | 10/1994 | Nady-Mohamed | |
| 5,409,496 | A | 4/1995 | Rowden et al. | |
| 5,431,662 | A | 7/1995 | Nicholas | |
| 5,520,698 | A | 5/1996 | Koh | |
| 5,540,700 | A | 7/1996 | Rowden et al. | |
| 5,549,563 | A | 8/1996 | Kronner | |
| 5,571,115 | A | 11/1996 | Nicholas | |
| 5,624,399 | A | 4/1997 | Ackerman | |
| 5,643,285 | A | 7/1997 | Rowden et al. | |
| 5,658,295 | A * | 8/1997 | Krementsov | 606/119 |
| 5,690,617 | A | 11/1997 | Wright | |
| 5,810,806 | A | 9/1998 | Ritchart et al. | |
| 5,835,657 | A | 11/1998 | Suarez et al. | |
| 5,840,077 | A | 11/1998 | Rowden et al. | |
| 5,865,729 | A * | 2/1999 | Meehan et al. | 600/207 |
| 5,876,357 | A | 3/1999 | Tomer | |
| 6,039,701 | A * | 3/2000 | Sliwa et al. | 600/588 |
| 6,068,121 | A | 5/2000 | McGlinch | |
| 6,068,581 | A * | 5/2000 | Anderson | 482/93 |
| 6,080,118 | A | 6/2000 | Blythe | |
| 6,159,170 | A | 12/2000 | Borodulin et al. | |
| 6,174,282 | B1 * | 1/2001 | Tan | 600/224 |
| 6,287,251 | B1 * | 9/2001 | Tan | 600/224 |
| 6,328,729 | B1 | 12/2001 | Jervis | |
| 6,348,036 | B1 | 2/2002 | Looney et al. | |
| 6,423,075 | B1 | 7/2002 | Singh et al. | |
| 6,468,232 | B1 * | 10/2002 | Ashton-Miller et al. | 600/591 |
| 6,524,259 | B2 | 2/2003 | Baxter-Jones et al. | |
| 6,651,992 | B1 | 11/2003 | Smith | |
| 6,682,100 | B2 | 1/2004 | Wood et al. | |
| 6,741,895 | B1 | 5/2004 | Gafni et al. | |
| 6,752,819 | B1 | 6/2004 | Brady et al. | |
| 6,932,759 | B2 | 8/2005 | Kammerer et al. | |
| 6,966,881 | B2 * | 11/2005 | Ben-Cnaan et al. | 600/591 |
| 7,052,453 | B2 | 5/2006 | Presthus et al. | |
| 7,189,234 | B2 * | 3/2007 | Zucherman et al. | 606/249 |
| D561,337 | S * | 2/2008 | Stripe | D24/140 |
| 7,334,503 | B1 | 2/2008 | Newman | |
| 7,628,791 | B2 * | 12/2009 | Garrison et al. | 606/51 |
| 7,713,216 | B2 | 5/2010 | Dubey et al. | |
| 7,749,176 | B2 | 7/2010 | Dubey et al. | |
| D638,322 | S * | 5/2011 | Teramoto | D10/73 |
| 8,079,963 | B2 * | 12/2011 | Rosenblatt | 600/591 |
| 2001/0021854 | A1 | 9/2001 | Donnez et al. | |
| 2003/0187334 | A1 | 10/2003 | Biswas | |
| 2003/0195386 | A1 | 10/2003 | Thierfeld et al. | |
| 2003/0220538 | A1 | 11/2003 | Jacquetin | |
| 2004/0230092 | A1 | 11/2004 | Thierfeld et al. | |
| 2005/0049509 | A1 | 3/2005 | Mansour et al. | |
| 2005/0065395 | A1 | 3/2005 | Mellier | |
| 2005/0085827 | A1 | 4/2005 | G. et al. | |
| 2006/0015001 | A1 | 1/2006 | Staskin et al. | |
| 2006/0089570 | A1 * | 4/2006 | Mansour et al. | 600/591 |
| 2006/0199994 | A1 | 9/2006 | Inman et al. | |
| 2006/0241652 | A1 | 10/2006 | Doll et al. | |
| 2007/0129615 | A1 | 6/2007 | Backman et al. | |
| 2007/0179410 | A1 | 8/2007 | Mahajan et al. | |
| 2007/0292478 | A1 * | 12/2007 | Youri | 424/430 |
| 2008/0021350 | A1 | 1/2008 | Bechtle et al. | |
| 2008/0033222 | A1 | 2/2008 | Feuer et al. | |
| 2008/0177204 | A1 | 7/2008 | Greenberg | |
| 2008/0221590 | A1 | 9/2008 | Ikeda et al. | |
| 2009/0131954 | A1 | 5/2009 | Christian et al. | |
| 2009/0318914 | A1 * | 12/2009 | Utley et al. | 606/33 |
| 2010/0049094 | A1 | 2/2010 | O'Brien et al. | |
| 2010/0106163 | A1 | 4/2010 | Blair et al. | |
| 2010/0152749 | A1 | 6/2010 | Von Pechmann et al. | |
| 2010/0168784 | A1 | 7/2010 | Pustilnik | |
| 2010/0179575 | A1 | 7/2010 | Von Pechmann et al. | |
| 2010/0274159 | A1 * | 10/2010 | Perle et al. | 600/591 |
| 2010/0280309 | A1 | 11/2010 | Von Pechmann | |
| 2011/0130769 | A1 | 6/2011 | Boebel et al. | |

FOREIGN PATENT DOCUMENTS

| | | |
|---|---|---|
| DE | 10341561 | 4/2005 |
| EP | 0400458 | 12/1990 |
| EP | 0890342 | 1/1999 |
| WO | WO 2008/074054 | 6/2008 |
| WO | WO 2009/078953 | 6/2009 |

OTHER PUBLICATIONS

"Laparoscopic Hysterectomy and Colpotomy Accessories for Use Exclusively with the RUMI System Uterine Manipulator," *CooperSurgical The KOH Colpotomizer System*; 2 pages; Oct. 2006.

Culligan et al., "Long-Term Success of Abdominal Sacral Colpopexy Using Synthetic Mesh," Am. J. Obstet. Gynecol., Dec. 2002.

* cited by examiner

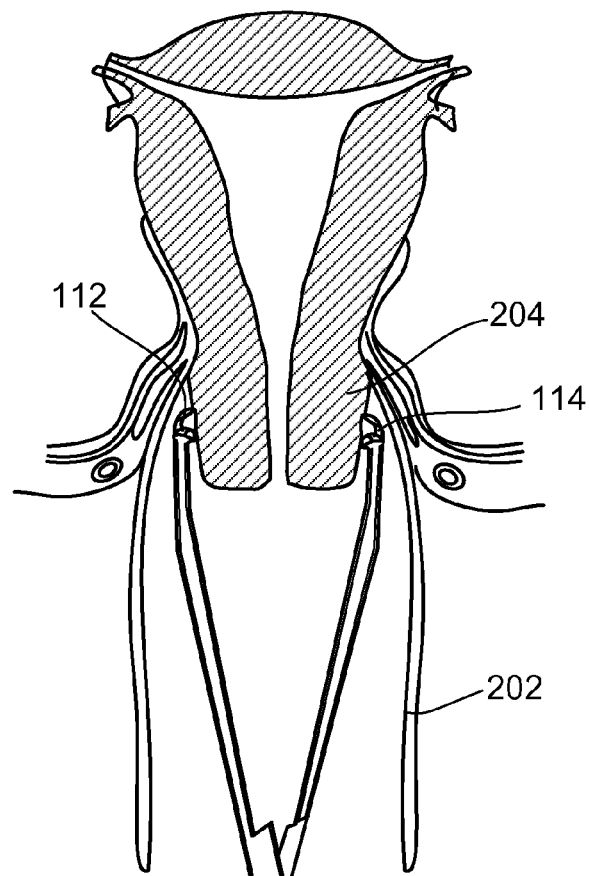
FIG. 9
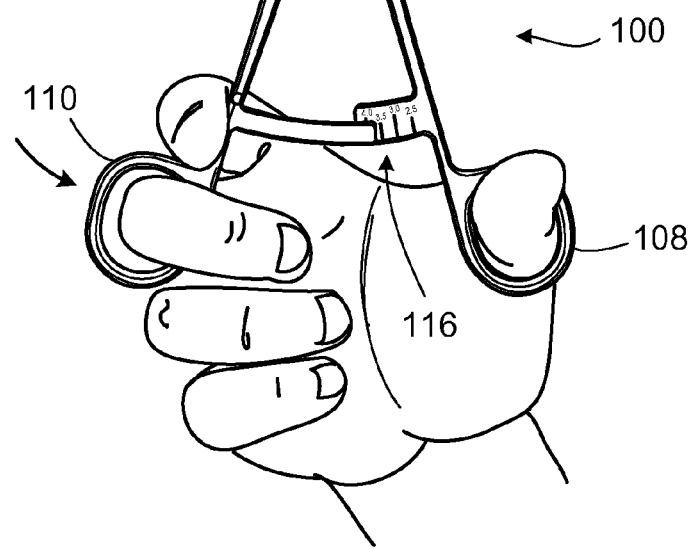

CERVICAL SIZING DEVICES AND RELATED KITS AND METHODS

CROSS-REFERENCE TO RELATED APPLICATIONS

This application is a continuation application of and claims priority to U.S. application Ser. No. 12/916,990, filed on Nov. 1, 2010, which is incorporated by reference herein.

TECHNICAL FIELD

This disclosure relates to cervical sizing devices and related kits and methods.

BACKGROUND

Uterine manipulators are medical instruments that are used for manipulating (e.g., moving or repositioning) a patient's uterus during medical procedures. Such procedures include surgical procedures such as laparoscopic gynecologic surgery, e.g., total laparoscopic hysterectomy (TLH) surgery.

Instruments of this kind often include a proximal portion that remains external to the patient's body during use and a distal portion that is inserted into the patient's body. The proximal portion typically provides for manipulation of the instrument during use. The distal portion often includes a tip that is sized to be inserted into and/or engage a uterus. Generally, the distal portion of the instrument is advanced through the vaginal cavity and into the uterus. With the distal portion inserted within a uterus, the uterus can be manipulated through surgeon or physician controlled movements of the proximal portion. During some surgical procedures, such as total laparoscopic hysterectomy (TLH) surgeries, a colpotomizer cup is attached to a distal end region of a uterine manipulator. The colpotomizer cup is configured to receive a portion of the patient's cervix during the procedure and can be used to assist the surgeon with properly identifying and on occasion incising the apex of the vagina. Following completion of a procedure, the instrument is typically removed from the patient's body via the vaginal cavity.

SUMMARY

In one aspect of the invention, a cervical sizing device includes first and second elongate arms that are pivotable about a pivot point relative to one another, first and second cervix contact members positioned at distal end regions of the first and second elongate arms, respectively, such that the first and second cervix contact members can be moved toward or away from one another as the elongate arms are pivoted about the pivot point relative to one another, and a measurement device positioned in a proximal portion of the cervical sizing device. The measurement device indicates an approximate size of a cervix when the cervix contact members are brought into contact with opposed outer surface regions of the cervix.

In another aspect of the invention, a kit includes multiple disposable medical devices that are configured to receive a cervix, and a cervical sizing device that includes first and second elongate arms that are pivotable about a pivot point relative to one another, first and second cervix contact members positioned at distal end regions of the first and second elongate arms, respectively, such that the first and second cervix contact members can be moved toward or away from one another as the elongate arms are pivoted about the pivot point relative to one another, and a measurement device positioned in a proximal portion of the cervical sizing device. The measurement device indicates an approximate size of a cervix when the cervix contact members are brought into contact with opposed outer surface regions of the cervix.

In an additional aspect of the invention, a method includes inserting a cervical sizing device into a patient in a manner such that a member of the cervical sizing device is disposed at least partially around a cervix of the patient to determine an approximate size of the cervix.

In a further aspect of the invention, a cervical sizing device includes an elongate arm and a member positioned at a distal end region of the elongate arm. The member is shaped to be positioned around at least a portion of an outer surface of a cervix, and the cervical sizing device can be used to determine an approximate size of a cervix when the member is brought into contact with an outer surface of the cervix.

In another aspect of the invention, a kit includes multiple cervical sizing devices, each of which includes a member shaped to be positioned around at least a portion of an outer surface of a cervix. The members of the cervical sizing devices differ in size such that the cervical sizing devices can be used to determine an approximate size of a cervix based on the size of the member that most closely conforms to an outer surface of the cervix when brought into contact with the outer surface of the cervix. The kit also includes multiple medical devices configured to receive a cervix of a patient, and each of the medical devices is a different size.

Implementations can include one or more of the following features.

In some implementations, the first and second cervix contact members are arcuate members.

In certain implementations, the arcuate members are sized to approximately conform to the outer surface of a cervix.

In some implementations, the measurement device includes first and second members that extend from the first and second elongate arms, respectively, and are configured to overlap one another as the first and second elongate arms are pivoted about the pivot point.

In certain implementations, at least one of the members of the measurement device includes a measurement scale that can be used to determine the approximate size of the cervix when the cervix contact members are brought into contact with the opposing outer surface regions of the cervix.

In some implementations, the measurement device includes a series of detents that allow the first and second members of the measurement device to be releasably fixed relative to one another in a plurality of different positions.

In certain implementations, the detents include a projection that extends from one of the members of the measurement device and a plurality of recesses formed in the other member of the measurement device, and each of the recesses is sized to receive at least a portion the projection therein.

In some implementations, the measurement device is configured to provide tactile feedback to a user of the cervical sizing device when the measurement device is moved into any one of the plurality of different positions.

In certain implementations, the measurement scale indicates a distance between the cervix contact members.

In some implementations, the measurement scale is printed on or engraved in one of the members of the measurement device.

In certain implementations, the measurement device is configured to releasably fix the cervical sizing device in a plurality of different positions such that the cervix contact members can be releasably fixed at a plurality of different distances of separation relative to one another.

In some implementations, the measurement device is configured to provide tactile feedback to a user of the cervical sizing device when the cervical sizing device is moved into one of the plurality of different positions from another of the plurality of different positions.

In certain implementations, the measurement device includes a measurement scale thereon that a user can use to determine an approximate size of the cervix.

In some implementations, the measurement scale includes only values that correspond to sizes of available medical devices.

In certain implementations, the medical devices are colpotomizer cups.

In some implementations, the cervical sizing device is configured such that the measurement device remains outside of a patient when the cervix contact members are positioned around a cervix of the patient.

In certain implementations, the cervical sizing device further includes first and second graspable loops extending from the first and second elongate arms, respectively, in a proximal end region of the cervical device.

In some implementations, each of the medical devices defines a cavity for receiving a cervix.

In certain implementations, the medical devices are uterine manipulator assembly components.

In some implementations, the uterine manipulator assembly components are colpotomizer cups.

In certain implementations, the method further includes, after determining the approximate size of the cervix, selecting a medical device defining a cavity configured to receive a cervix, and a size of the cavity of the selected medical device is approximately equal to the determined size of the cervix.

In some implementations, the method further includes inserting a proximal end region of a rod of the cervical sizing device into a uterus of the patient to determine an approximate depth of the uterus, and the member of cervical sizing device is attached to a distal end region of the rod.

In certain implementations, the method further includes, based on the determined approximate depth of the uterus, selecting a medical device for insertion into the uterus.

In some implementations, the member is a ring-shaped member.

In certain implementations, the member is an arcuate member.

In some implementations, the member is a ring segment.

In certain implementations, the arcuate member includes a curved segment and substantially straight segments that extend approximately tangentially from ends of the curved segment.

In some implementations, the member has a radius of curvature, and the approximate size of the cervix can be determined based on the radius of curvature of the member.

In certain implementations, a proximal end region of the elongate arm includes a uterus depth measurement scale.

In some implementations, the member of each cervical sizing device is a ring-shaped member.

In certain implementations, the member of each cervical sizing device is an arcuate member.

In some implementations, the member of each cervical sizing device is a ring segment.

In certain implementations, each arcuate member includes a curved segment and substantially straight segments that extend approximately tangentially from ends of the curved segment.

In some implementations, the member of each cervical sizing device has a radius of curvature, and the approximate size of the cervix can be determined based on the radii of curvature of the members.

In certain implementations, each of the cervical sizing devices further includes an elongate arm, and the member of each cervical sizing device is positioned at a distal end region of the elongate arm.

In some implementations, a proximal end region of the elongate arm includes a uterus depth measurement scale.

In certain implementations, the kit further includes an elongate arm configured to be releasably attached to each of the members.

In some implementations, each of the medical devices defines a cavity for receiving a cervix.

In certain implementations, the medical devices are uterine manipulator assembly components.

In some implementations, the uterine manipulator assembly components are colpotomizer cups.

Implementations can include one or more of the following advantages.

In some implementations, the cervical sizing device allows the user to determine the approximate size of the patient's cervix and subsequently select an appropriately sized medical device (e.g., an appropriately sized colpotomizer cup, pessary, or other gynecological or obstetrical devices) without having to first insert the medical device into the patient. As a result, it is possible to reduce the number of medical devices that are inserted into the patient for sizing purposes and then not used during the procedure. The cervical sizing device can be particularly advantageous when the medical device to be selected is disposable. In such a case, if an incorrectly sized medical device is inserted into the patient and needs to be replaced with another component of a different size, the incorrectly sized component would typically need to be discarded as it would have become contaminated by the patient's bodily fluids. Needlessly discarding medical devices in this way can be costly to the physician and the patient.

In certain implementations, the cervical sizing device is sized and shaped to be more easily inserted into the patient's vagina and positioned around the outer surface of the cervix than a medical device for which the cervix is being sized (e.g., a colpotomizer cup). Thus, using the cervical sizing device to determine the approximate size of the cervix can be easier and faster than determining the approximate size of the cervix with the medical device itself.

In some implementations, the cervical sizing device is adjustable such that a single cervical sizing device can be used to approximate the size of any of various different cervixes having different sizes. As a result, the amount of time required to approximate the size of the patient's cervix can be reduced since there is typically no need to determine which cervical sizing device is appropriate for a particular patient. Additionally, the cost involved with such procedures can be reduced because fewer cervical sizing devices may be used during such procedures.

In certain implementations, the adjustable cervical sizing device is provided with a measurement scale on a proximal end region of the cervical sizing device (i.e., on a portion of the cervical sizing device that remains outside of the patient during the sizing procedure). By providing the measurement scale on the portion of the cervical sizing device that remains outside of the patient, the user can determine the size of the cervix without having to closely analyze the portion of the cervical sizing device disposed around the cervix.

In some implementations, the cervical sizing device is configured to be temporarily fixed or locked (e.g., mechanically fixed or locked) in certain positions to facilitate accurate sizing of the cervix. This temporary fixing or locking function can, for example, be carried out by a series of detents. For example, the cervical sizing device can include overlapping members, and one of the overlapping members can include a projection that becomes engaged in a series of recesses formed in the other overlapping member as the portion of the cervical sizing device surrounding the cervix is expanded and retracted. By temporarily fixing or locking the cervical sizing device at various different positions corresponding to different cervix sizes, the user of the cervical sizing device is more easily able to read a measurement scale provided on the cervical sizing device.

In certain implementations, the mechanism that temporarily fixes the cervical sizing device in the various different positions provides tactile and/or audible feedback to the user as the cervical sizing device is moved from one position to the next. This feedback can help the user to determine the size of the cervix being measured. In some cases, the user might even be able to use only the tactile and/or audible feedback to determine the size of the cervix without having to consult a visual aid (e.g., a measurement scale) on the cervical sizing device.

In some implementations, the values provided on the measurement scale of the cervical sizing device are the same as the values associated with various different medical devices designed to engage the cervix of a patient during use (e.g., various different colpotomizer cups, pessaries, or other gynecological or obstetrical devices) that can be used during a medical procedure. The measurement scale can, for example, include only values that correspond to the sizes of particular medical devices available for use in a procedure. As a result, the user can easily determine the appropriate medical device to use without having to perform additional calculations, approximations, or numerical conversions.

Other aspects, features, and advantages of the invention will be apparent from the description and drawings, and from the claims.

DESCRIPTION OF DRAWINGS

FIGS. 7-9 illustrate a method of using the cervical sizing device of FIG. 1 to determine the approximate size of a patient's cervix.

DETAILED DESCRIPTION

Figure 1:
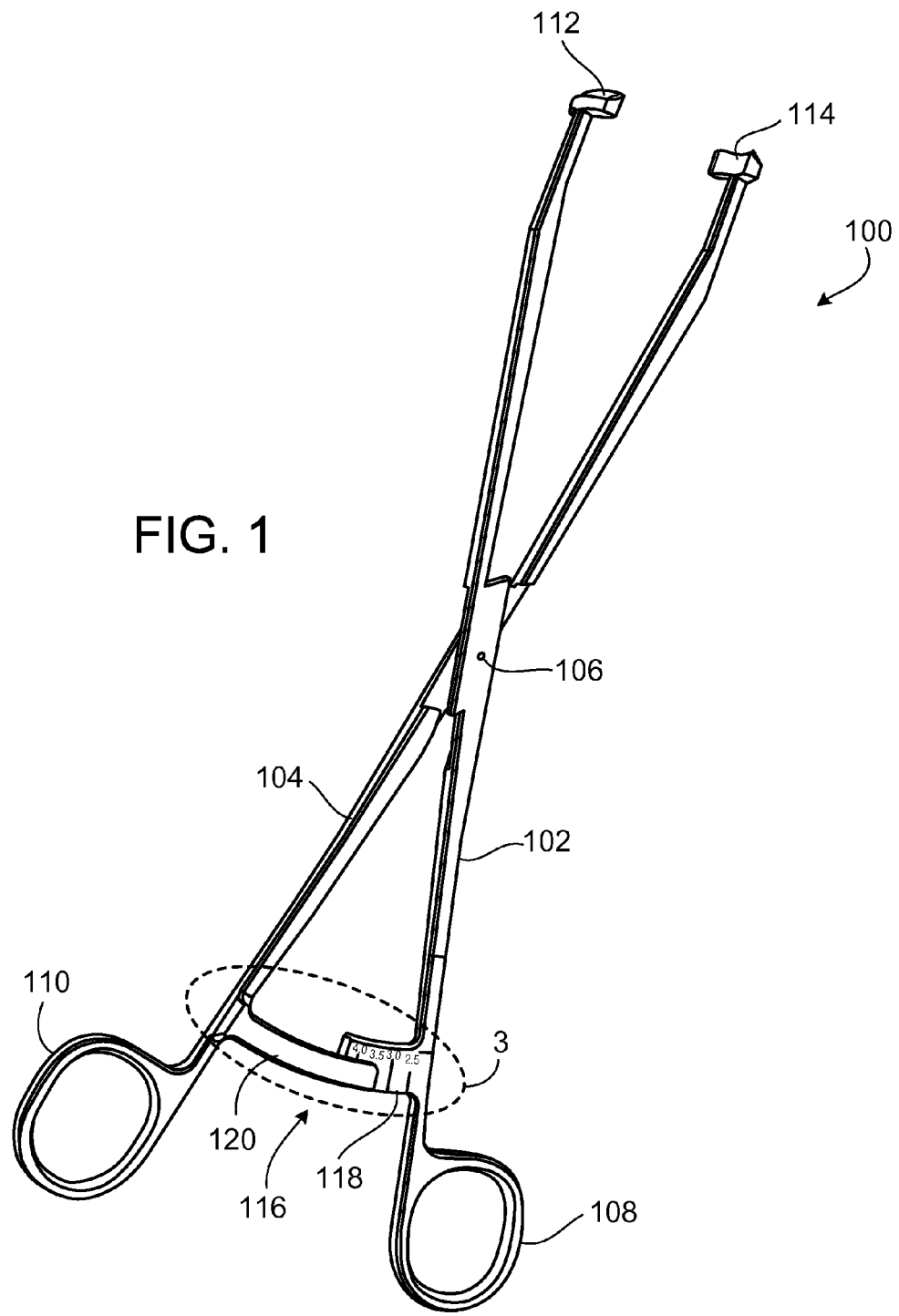
FIG. 1 is a front, perspective view of an adjustable cervical sizing device that includes pivotable arms and arcuate members positioned near a distal end region of each arm.
Figure 2:
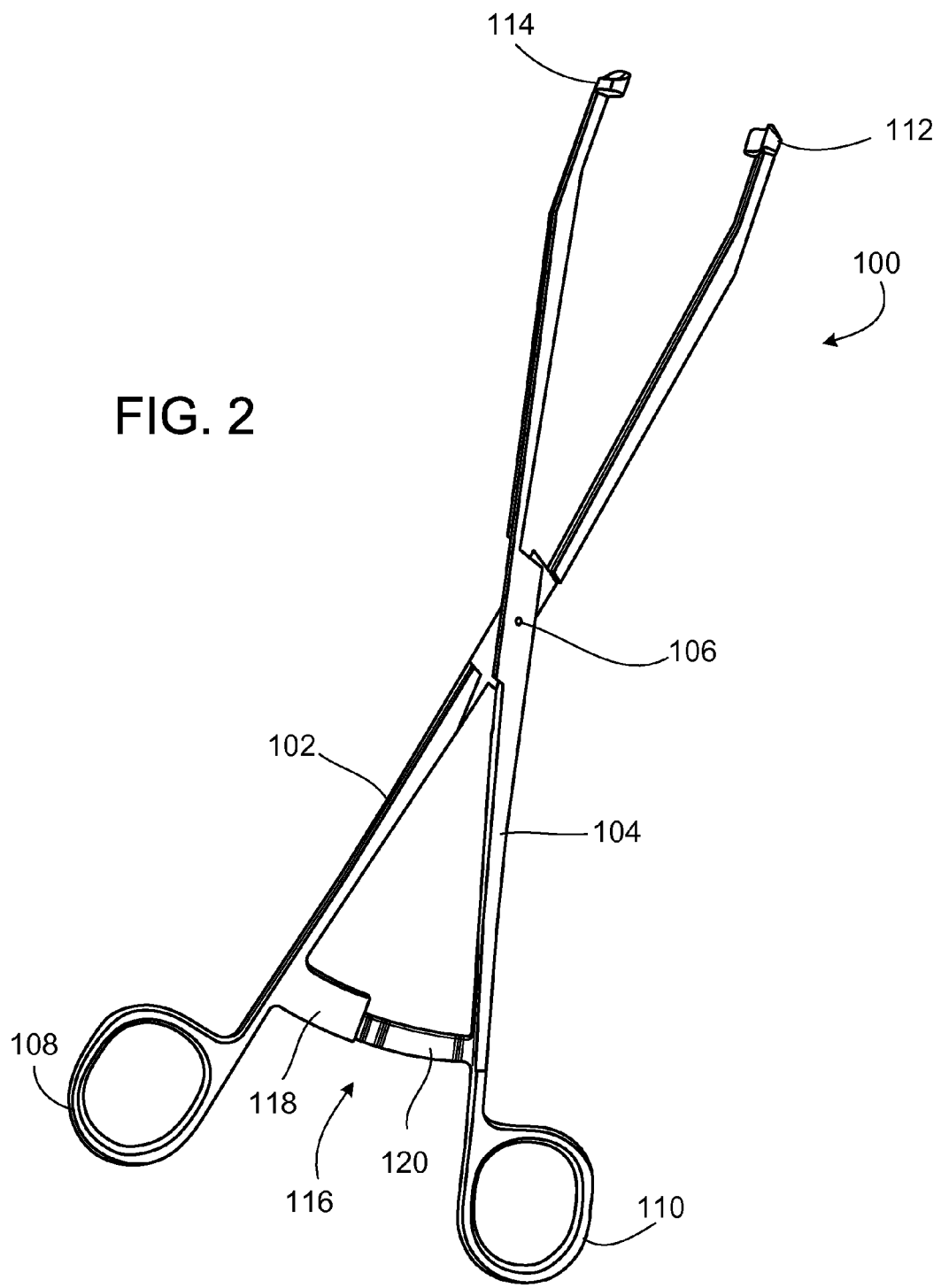
FIG. 2 is a rear, perspective view of the adjustable cervical sizing of FIG. 1.

Referring to FIGS. 1 and 2, a cervical sizing device 100 includes first and second elongate arms 102, 104 that are pivotably connected to one another via a pin 106. Near a distal end of the cervical sizing device 100, arcuate contact pads 112, 114 extend from the elongate arms 102, 104. Graspable loops 108, 110 extend from the elongate arms 102, 104 near a proximal end of the cervical sizing device 100. The graspable loops 108, 110 are sized so that a user can insert his or her thumb through one of the loops 108, 110 and his or her finger through the other of the loops 108, 110 to operate the device. The proximal end region of the cervical sizing device 100 also includes a measurement mechanism 116. The cervical sizing device 100 can be used to determine an approximate size (e.g., approximate outer diameter) of a patient's cervix. To determine the approximate size of the patient's cervix, the user grasps the cervical sizing device 100 by inserting his or her thumb and finger through the graspable loops 108, 110 and then inserts the distal portion of the cervical sizing device 100 into the patient's vagina. The user then manipulates the cervical sizing device 100 to position the arcuate contact pads 112, 114 about the outer surface of the patient's cervix in a manner such that the arcuate contact pads 112, 114 are in contact with substantially opposite sides of the patient's cervix. With the cervical sizing device 100 in this configuration, the user views the measurement mechanism 116, which remains outside of the patient along with the graspable loops 108, 110, to determine the approximate size of the patient's cervix. As will be discussed below, determining the size of the patient's cervix in this manner allows the user to quickly and easily select uterine manipulator device components, such as colpotomizer cups, that are suitably sized for use in a subsequent medical procedure for that particular patient.

Figure 3:
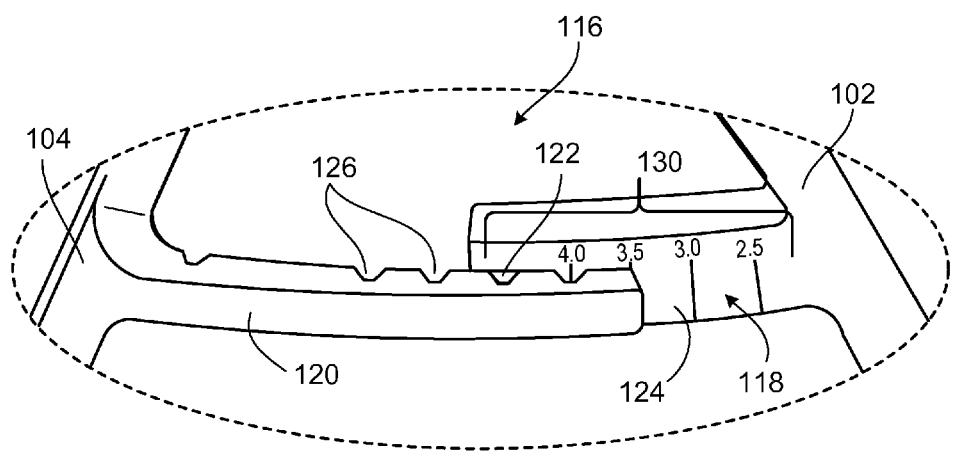
FIG. 3 is an enlarged view of region 3 in FIG. 1, which illustrates a measurement mechanism that bears a measurement scale and is positioned near a proximal end region of the cervical sizing device of FIG. 1.
Figure 4:
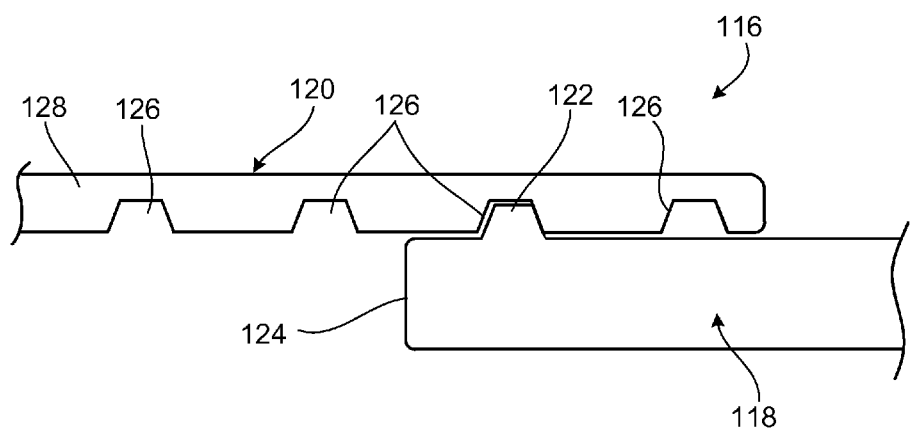
FIG. 4 is a bottom view of the measurement mechanism of the cervical sizing device of FIG. 1.

As shown in FIG. 3, which is an enlarged view of the measurement mechanism 116, and FIG. 4, which is an upward looking bottom view of the measurement mechanism 116, the measurement mechanism 116 includes first and second mating components 118, 120 that extend from the elongate arms 102, 104. The first component 118 includes a projection 122 extending from a base 124. The projection 122 is substantially triangular or semi-hexagonal in cross-section. The second component 120 includes a series of four recesses 126 formed in a base 128. The recesses 126 are substantially triangular or semi-hexagonal voids that are sized to receive the projection 122 or a portion of the projection 122. Each position at which the projection 122 is disposed within one of the recesses 126 corresponds to a different distance of separation between the arcuate contact pads 112, 114, and thus a different cervix size of a patient when the cervical sizing device 100 is being used to measure the cervix size of different patients.

As shown in FIG. 3, a measurement scale 130 is printed and/or engraved on the base 124 of the first component 118. The measurement scale 130 includes four different markings, namely "2.5," 3.0," "3.5," and "4.0," which correspond to the four different fixed distances of separation (in centimeters in this case) between the arcuate contact pads 112, 114 of the cervical sizing device 110. More specifically, each marking represents a distance between the arcuate contact pads 112, 114 when the projection 122 of the first component 118 is disposed in one of the four different recesses 126 formed along the second component 120. For example, when the projection 122 of the first component 118 is disposed in the recess 126 of the second component 120 that corresponds to the arcuate contact pads 112, 114 being 3.5 centimeters apart, as shown in FIG. 3, the free end of the second component 120 is aligned with the line of the measurement scale 130 associate with the "3.5" marking on the measurement scale 130. The free end of the second component 120 would similarly align with the line associated with one of the other three numerical markings of the measurement scale 130 when the projection 122 of the first component 118 is disposed within one of the other three recesses 126 of the second component 120. As a result, the user of the cervical sizing device 100 can quickly and easily determine the distance of separation between the arcuate contact pads 112, 114, and thus the diameter of the cervix of the patient in which the cervical sizing device 100 is being used.

The projection 122 and the recesses 126 are configured to form a series of detents that allow the first and second components 118, 120 of the measurement mechanism 116 to be slid relative to one another, from one position to the next position (e.g., from the "4.0" position to the "3.5" position), with relatively little force. For example, the projection 122 of the first component 118 can be dislodged from one of the recesses 126 of the second component 120 by applying a squeezing force of no greater than about 2.0 lbf (e.g., no greater than 0.5 lbf) to the graspable loops 108, 110 of the cervical sizing device 100. In certain implementations, for example, a force of about 0.25 lbf to about 2.0 lbf (e.g., about 0.5 lbf to about 1.5 lbf) is required to move the cervical sizing device 100 from one position to the next. Permitting operation of the cervical sizing device 100 with the relatively low squeezing forces described above helps to ensure that the device provides accurate positioning data to the user in a safe and efficient manner by helping to reduce or minimize abrupt, uncontrolled movements of the first and second components 118, 120 of the measurement mechanism 116 relative to one another.

Because the projection 122 snaps into and out of engagement with the series of recesses 126 when the cervical sizing device 100 is expanded and contracted (i.e., when the arcuate contact pads 112, 114 are moved away from one another and toward one another, respectively), the measurement mechanism 116, in addition to providing a visual indication of the distance of separation of the between the arcuate contact pads 112, 114, provides tactile feedback to the user to indicate that the cervical sizing device 100 has been moved from one position, such as the "4.0" position, into another position, such as the "3.5" position. In particular, as the projection 122 snaps into engagement with one of the recesses 126, the vibration or force associated with that engagement is transmitted to the thumb and finger of the user via the elongate arms 102, 104 and graspable loops 108, 110. Thus, even if for some reason the markings on the measurement scale 130 are difficult to read during a particular sizing procedure, the user is informed of the cervix size by feeling the number of transitions from one position to the next. Also, even when the measurement scale 130 is clearly visible to the user, which will typically be the case, the tactile feedback that the user experiences provides a redundant technique for determining the size of the cervix, and can thus help to prevent errors resulting from misreading the position of the cervical sizing device 100 visually indicated by the measurement mechanism 116.

Similar to the tactical feedback described above, in certain implementations, the cervical sizing device 100 is constructed to provide audible feedback to the user as the cervical sizing device 100 is transitioned from one position to the next. For example, as the projection 122 snaps into engagement with one of the recesses 126, the abrupt contact between the projection 122 and the portion of the second component 120 that forms the recess 126 can make a noise loud enough to be heard by the user. This configuration can supply yet another technique by which the user can determine the position of the cervical sizing device 100 and thus the size of a patient's cervix.

Still referring to FIG. 3, in some implementations, the projection 122 has a maximum height (measured from the apex of the projection 122 to the surface of the base 124 from which the projection extends) of about 2.0 millimeters and a width that tapers from about 1.0 millimeter at the apex of the projection 122 to about 6.0 millimeters at the surface of the base 124 from which the projection 122 extends. Similarly, each of the recesses 126 can have a maximum depth of about 2.0 millimeters and a width that tapers from about 1.0 millimeter to about 6.0 millimeters. It has been found that these dimensions allow the cervical sizing device 100 to be moved from one position to the next with relatively little force, as described above.

Figure 5:
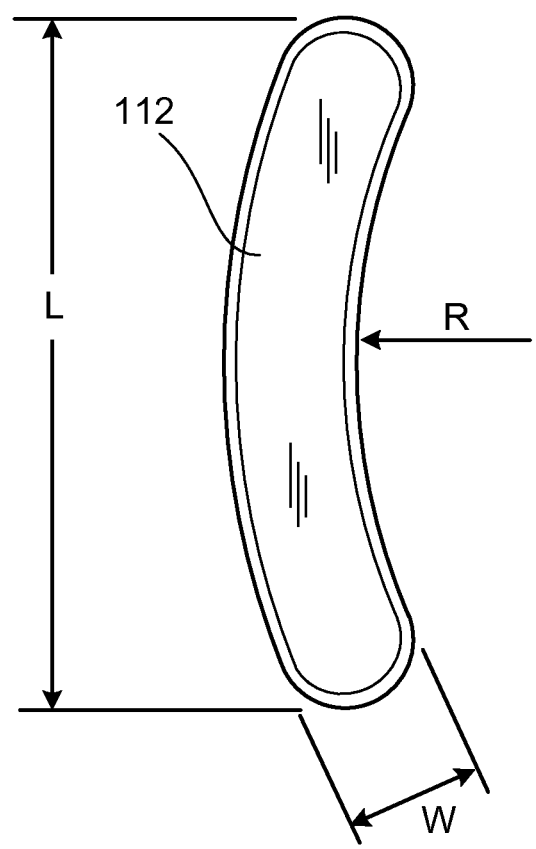
FIG. 5 is an end view of one of the arcuate members of the cervical sizing device of FIG. 1.

FIG. 5 is an enlarged end view of the arcuate contact pad 112. Because the arcuate members 112 and 114 are substantially identical, only the member 112 will be described in detail here. The arcuate contact pad 112 is shaped to roughly correspond to the outer surface of the cervix. For example, the arcuate contact pad 112 typically has a radius of curvature R of about 1.0 centimeters to about 2.0 centimeters. It is believed that most cervixes with which the cervical sizing device 100 will be used will have an outer diameter of about 2.0 centimeters to about 4.0 centimeters. Therefore, the arcuate contact pad 112 will comfortably receive most cervixes. The length of the arcuate contact pad 112 can range from about 20 degrees to about 180 degrees. In certain implementations, the arcuate contact pad 112 has a length L of about 0.75 inch and a width W of about 0.125 inch.

The cervical sizing device 100 is sized such that the proximal portion of the device, including the measurement mechanism 116, remains outside of the patient and visible to the user when the distal portion of the device is inserted into the patient and the contact pads 112, 114 are positioned around the patient's cervix. In some implementations, the cervical sizing device 100 has a length of about 8 inches to about 12 inches (e.g., about 10 inches).

Referring briefly again to FIGS. 1 and 2, the cervical sizing device 100 is typically formed of a medical grade metal, such as stainless steel. This allows the cervical sizing device 100 to be re-used after being sterilized. However, the cervical sizing device 100 can alternatively be formed of medical grade plastic, such as polycarbonate. In such cases, the cervical sizing device 100 can be a single use device that is disposed of after the sizing procedure.

Any of various techniques can be used to manufacture the cervical sizing device 100 and its separate components. Generally, the elongate arm 102 and its associated graspable loop 108 and arcuate contact pad 112 are integrally formed (e.g., injection molded or die cast), and the other elongate arm 104 is similarly integrally formed (e.g., injection molded or die cast) with its associated graspable loop 110 and arcuate contact pad 114. After forming the elongate arms 102, 104 and their associated graspable loops 108, 110 and arcuate contact pads 112, 114, the elongate arms 102, 104 are secured to one another by fixing the pin 106 through holes formed in the central region of each elongate arm 102, 104. As an alternative to integrally forming the elongate arms 102, 104 with their associated components (i.e., the graspable loops 108, 110 and the arcuate contact pads 112, 114), those associated components can be separately formed and then attached (e.g., welded) to the elongate arms 102, 104. Also, while the elongate arms 102, 104 and associated components have been described as being formed using a molding technique, such as injection molding or die casting, they can alternatively be formed using other techniques, such as machining techniques.

Figure 6:
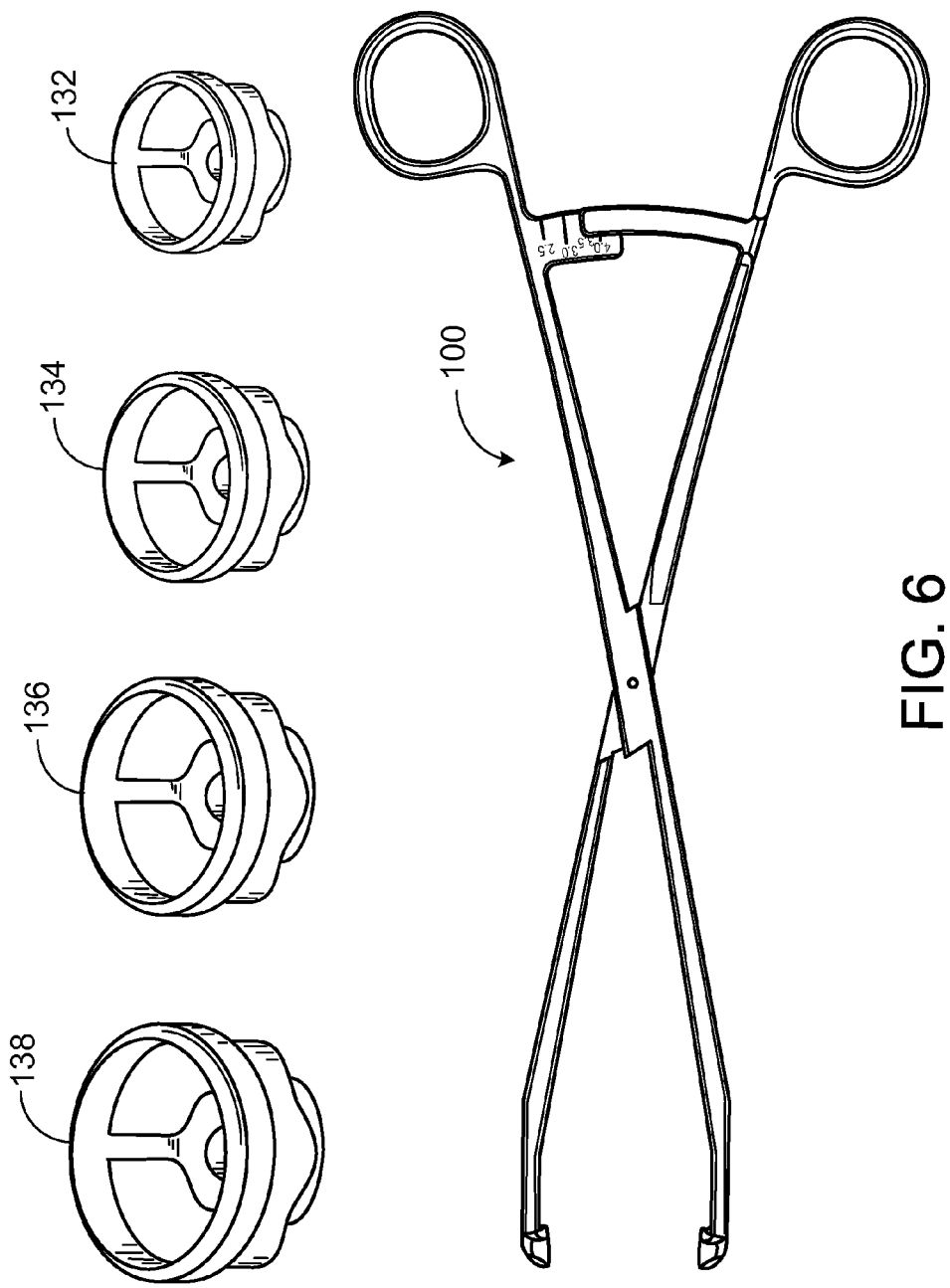
FIG. 6 illustrates a kit that includes the cervical sizing device of FIG. 1 and multiple different sized colpotomizer cups.

FIG. 6 illustrates a kit that includes the cervical sizing device 100 and four different sized colpotomizer cups 132, 134, 136, 138. In this case, the four colpotomizer cups 132, 134, 136, 138 have inner diameters of 2.5 centimeters, 3.0 centimeters, 3.5 centimeters, and 4.0 centimeters, respectively. In some implementations, the colpotomizer cups are designed as reusable devices that can be sterilized after each use. In other implementations, the colpotomizer cups are designed as single use, disposable devices that are discarded after use. Suitable colpotomizer cups are available from CooperSurgical, Inc. (Trumbull, Conn.), under the name KOH Cups™.

Figure 7:
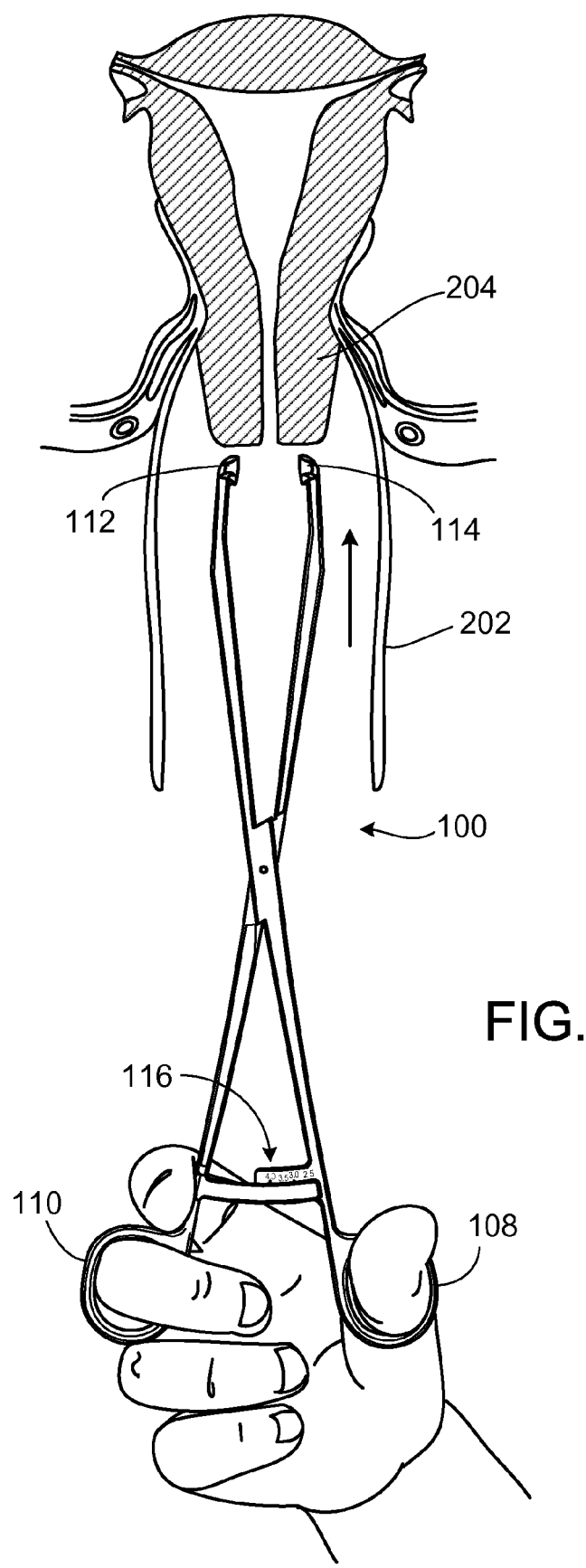
Figure 8:
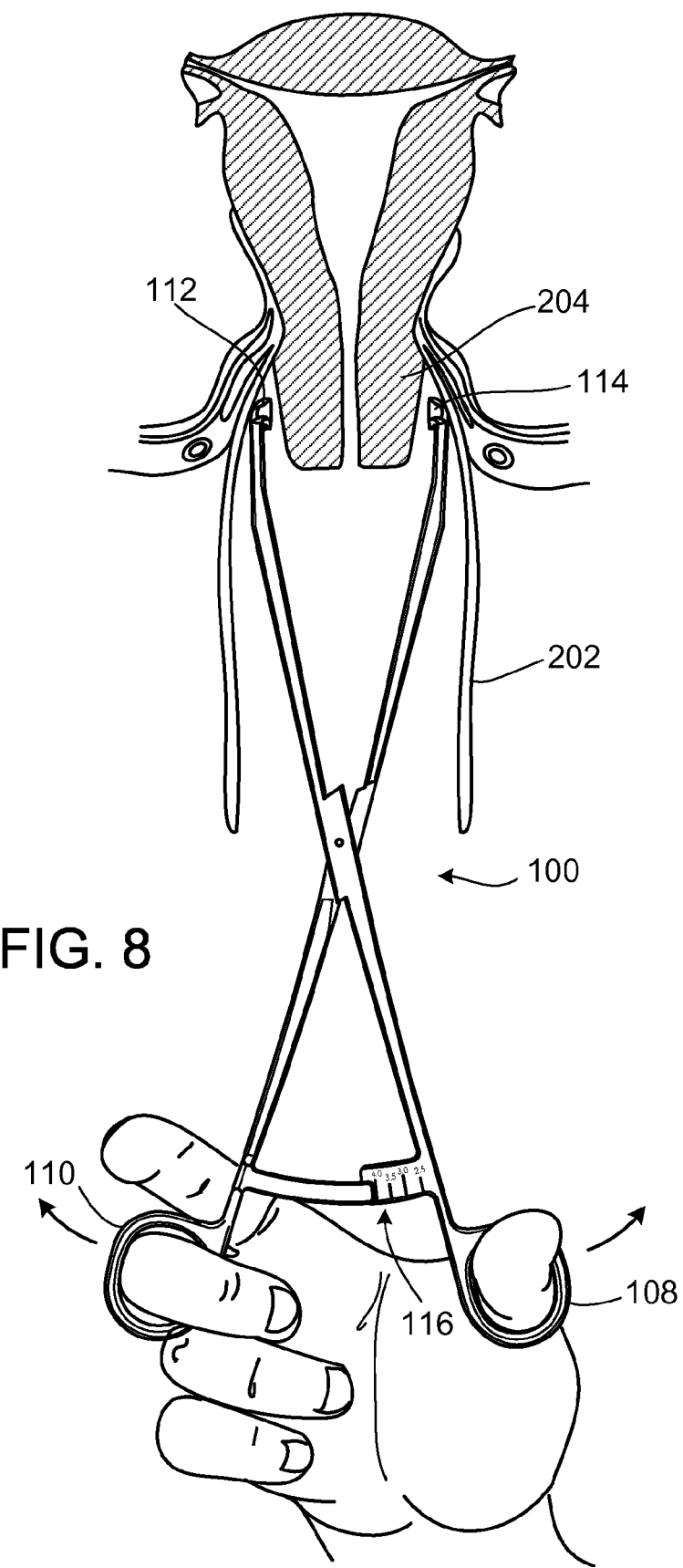

FIGS. 7-9 illustrate a method of using the cervical sizing device 100 to determine the approximate size of a patient's cervix. As shown in FIG. 7, the user first grasps the cervical sizing device 100 with his or her thumb and middle finger and, with the cervical sizing device 100 in the fully contracted or closed position (i.e., with the arcuate contact pads 112, 114 in contact with one another), inserts the device into the vagina 202 of the patient. While inserting the cervical sizing device 100 and throughout the sizing procedure, the vagina 202 of the patient is typically held in an expanded state using a vaginal retracting device, such as a vaginal speculum. This allows the user to see inside the patient's vaginal cavity during the sizing procedure.

The user advances the cervical sizing device 100 into the patient until the distal end of the device has almost reached the cervix 204 of the patient. At this point, the user spreads his or her thumb and middle finger apart to move the graspable loops 108, 110, and thus the arcuate contact pads 112, 114, away from one another and further advances the cervical sizing device 100 into the patient such that the spread apart arcuate contact pads 112, 114 are positioned around and on opposite sides of the portion of the cervix 204 that extends into the vagina 202 (i.e., the portion of the cervix 204 at the level of the vaginal fornix), as shown in FIG. 8.

Referring to FIG. 9, after positioning the arcuate contact pads 112, 114 on opposite sides of the cervix 204, the user squeezes the graspable loops 108, 110 together until the arcuate contact pads 112, 114, which are similarly caused to move together, are gently brought into contact with the outer surface of the cervix 204, on opposite sides of the cervix 204. Once the user has visually confirmed that the arcuate contact pads 112, 114 are in contact with the outer surface of the cervix 204, the user views the measurement mechanism 116 of the cervical sizing device 100 to determine the approximate size (i.e., the approximate outer diameter) of the portion of the cervix 204 contacted by the arcuate contact pads 112, 114.

After noting the approximate size of the patient's cervix 204, the user again spreads the arcuate contact pads 112, 114 by moving the graspable loops 108, 110 away from one another and retracts the cervical sizing device 100 away from the cervix 204. After clearing the cervix 204, the user contracts the distal end of the cervical sizing device 100 by squeezing the graspable loops 108, 110 together and continues to retract the cervical sizing device 100. Contracting the cervical sizing device 100 in this manner reduces the overall volume of the device by bringing the arcuate contact pads 112, 114 into close proximity to (e.g., into contact with) one another and thus facilitates passage of the device through the patient's vagina 202. The user continues to retract the cervical sizing device 100 until the device has been entirely removed from the patient at which point the user sets the cervical sizing device 100 aside for sterilization or, in the case of a single-use device, discards the cervical sizing device 100.

The user then selects the disposable colpotomizer cup 132, 134, 136, 138 (shown in FIG. 6) that most closely corresponds to the determined size of the patient's cervix 204. For example, if the cervix 204 of the patient was determined to have an outer diameter of about 3.5 centimeters, the user would select the colpotomizer cup 134, which has an inner diameter of about 3.5 centimeters. The user would then attach the colpotomizer cup 134 to a uterine manipulator for performing a subsequent surgical procedure, such as a hysterectomy. By using the cervical sizing device 100 to determine the size of the patient's cervix 204, the likelihood of initiating the surgical procedure with an improperly sized colpotomizer cup is reduced or minimized. This is particularly advantageous in those situations in which the colpotomizer cups are single use, disposable devices because, if it is not determined that the selected disposable colpotomizer cup is the incorrect size until after the selected disposable colpotomizer cup has been removed from its sterile packaging, the cup would need to be discarded, which is wasteful and costly to the patient and the user. And, even in the case of reusable colpotomizer cups, using the cervical sizing device 100 to determine the size of the patient's cervix 204 prior to selecting the colpotomizer cup to be used in the subsequent surgical procedure can increase the speed and efficiency with which the surgical procedure is performed. The use of the cervical sizing device 100 can, for example, help to prevent a scenario in which an incorrectly sized colpotomizer cup is initially selected for the procedure and then needs to be exchanged for a the correctly sized colpotomizer cup, which can be relatively cumbersome and time consuming.

After selecting the appropriately sized colpotomizer cup, the colpotomizer cup can be attached to a uterine manipulator for use during a subsequent medical procedure. Examples of certain uterine manipulator assemblies, which include a uterine manipulator and a colpotomizer cup, and uses of such uterine manipulator assemblies are described in U.S. patent application Ser. No. 12/565,367, filed on Sep. 23, 2009, and entitled "Uterine Manipulator Assemblies and Related Components and Methods," which is incorporated by reference herein.

While certain implementations have been described above, other implementations are possible. For example, while the cervical sizing device 100 has been described as being configured to stop at positions 2.5, 3.0, 3.5, and 4.0 and the measurement scale 130 has been described as including those same values, it should be understood that the cervical sizing device can be configured to stop at any of various different positions depending on available sizes of the medical devices (e.g., colpotomizer cups) for which the cervix is being sized, and the measurement scale can include values corresponding to those positions. For example, in cases where additional sizes of medical devices are available for use, the cervical sizing device can be configured to stop at additional positions, and the measurement scale can include values corresponding to those positions. Similarly, in cases where fewer sizes of medical devices are available for use, the cervical sizing device can be configured to stop at fewer positions, and the measurement scale can include values corresponding only to those positions. Further, in cases in which the medical devices are only available in sizes that differ from those sizes associated with the cervical sizing device 100, the cervical sizing device would be configured differently to stop at positions corresponding to those different sizes, and the measurement scale would be labeled with the different sizes.

While the measurement scale 130 of the measurement mechanism 116 has been described as including only equally spaced numerical values each of which corresponds to the size of an available colpotomizer cup that may be used during a surgical procedure, other types of measurement scales can be used. For example, in cases in which the available colpotomizer cups only come in unequally spaced sizes (e.g., 2.5 centimeters, 3.0 centimeters, and 4.0 centimeters), the measurement scale can include only the unequally spaced numerical values that correspond to those available sizes. In addition, in such cases, the second component 120 of the measurement mechanism 116 can include recesses positioned to correspond only to those unequally spaced positions. This can simplify the sizing process for the user.

Similarly, in certain implementations, the measurement mechanism includes a graduated scale of numerical values, which includes numerical values in addition to those that correspond to available sizes of colpotomizer cups. In such cases, the measured diameter of the patient's cervix would be compared to the various colpotomizer cups available for use to select the most appropriate colpotomizer cup to be used with that particular patient. Such measurement mechanisms can, in some cases, advantageously allow for a more accurate determination of the size of the patient's cervix and can allow the cervical sizing device to be used to determine the cervix size for reasons other than selected a correspondingly sized colpotomizer cup. These measurement mechanisms can, for example, allow a user to select other types of medical devices that are intended to engage the cervix and are available in different sizes.

While the measurement mechanism 116 has been described as having a printed or engraved measurement scale 130 that the user reads to determine the approximate size of a patient's cervix, other types of measurement devices can be used. In certain implementations, for example, electronic measurement devices are used. Examples of such devices include digital calipers and micrometers.

While the projection 122 of the measurement device 116 has been described as being substantially triangular or semi-hexagonal in cross-section and the recesses 126 of the measurement device 116 have been described as being substantially triangular or semi-hexagonal, the projection 122 and recesses 126 can have any of various other substantially matching shapes. For example, the projection 122 and recesses 126 can alternatively be semi-circular or rectangular in cross-section.

Figure 10:
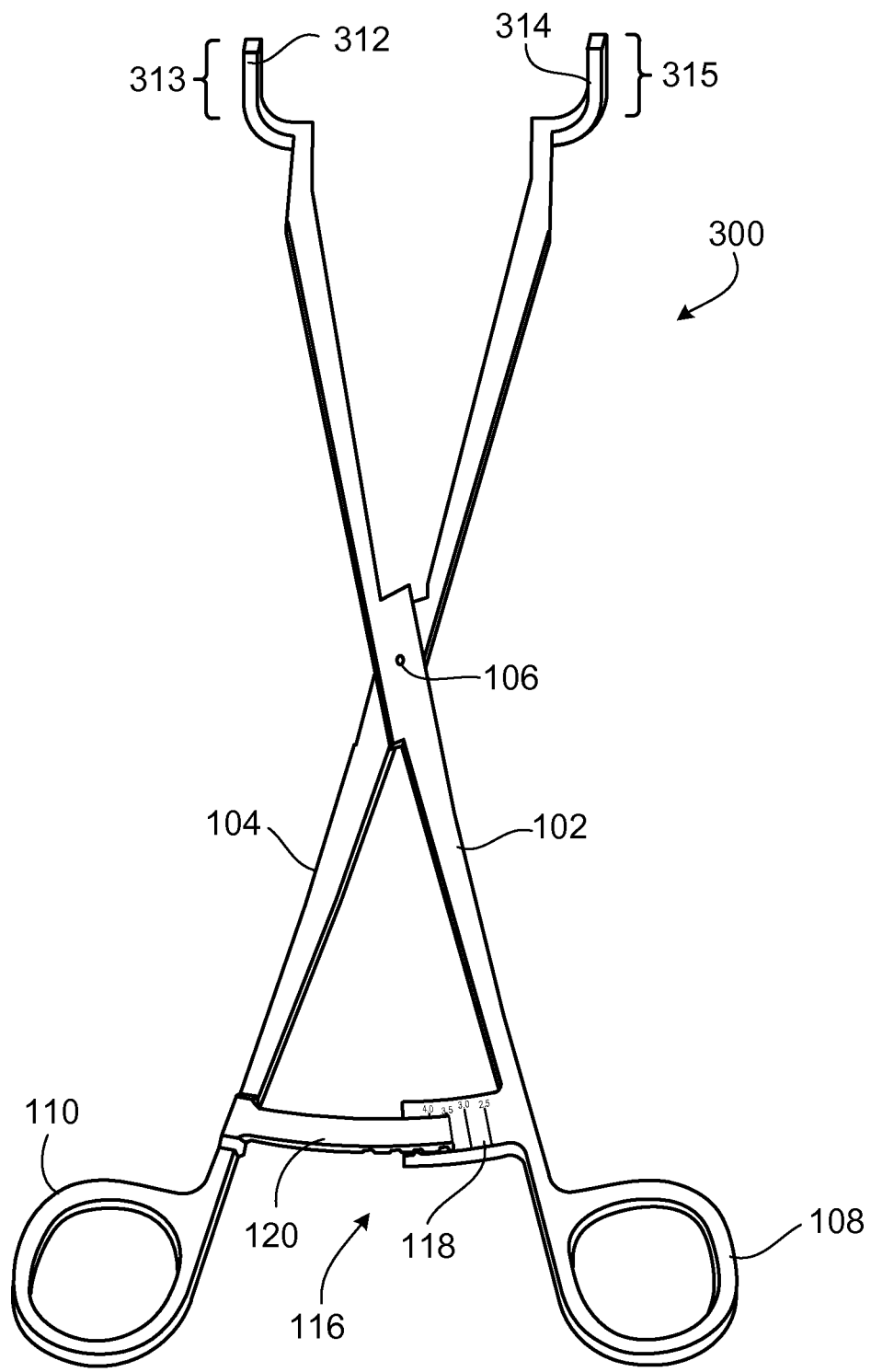
FIG. 10 is a front, perspective view of an adjustable cervical sizing device that includes pivotable arms and arcuate members, where each arcuate member is secured in one of its end regions to a distal end region of one of the arms.

While the arcuate contact pads 112, 114 have been described as having central portions attached to the distal ends of the elongate arms 102, 104, in certain implementations, an end region of each of the contact pads is attached to the distal end of its associated elongate arm. In addition, while the arcuate contact pads 112, 114 have been described as having a constant radius of curvature, in some implementations, a straight member can extend from the free end of each arcuate contact pad to provide improved visibility for the user. As shown in FIG. 10, for example, an adjustable cervical sizing device 300 includes arcuate contact pads 312, 314 that are attached in their end regions to the distal ends of the elongate arms 102, 104. Apart from the arcuate contact pads 312, 314, the cervical sizing device 300 is generally the same as the cervical sizing device 100 described above. The arcuate contact pads 312, 314 extend substantially perpendicularly from the arms 102, 104. Unlike the arcuate contact pads 112, 114 that were described as being attached in their central regions to the elongate arms 102, 104, the arcuate contact pads 312, 314 are attached in their end regions to the elongate arms 102, 104. In addition, unlike the arcuate contact pads 112, 114 that were illustrated as having substantially constant radii of curvature, the arcuate contact pads 312, 314 include substantially straight segments 313, 315 that extend substantially tangentially from the free ends of curved portions of the arcuate contact pads 312, 314.

Because the arcuate contact pads 312, 314 extend outwardly to one side of the arms 102, 104, the user is better able to view the engagement of the curved portions of those arcuate contact pads 312, 314 with a cervix of a patient. In particular, as the user looks along the length of the cervical sizing device 300, the user's view of the arcuate contact pads 312, 314 will not be obstructed or will be only minimally obstructed by the arms 102, 104 of the device. The straight segments 313, 315 extending from the curved portions of the arcuate contact pads 312, 314 further increase the user's ability to view contact between the arcuate contact pads 312, 314 and the patient's cervix by extending that pads 312, 314 further outward from the arms 102, 104 and thus decreasing the likelihood of the arms 102, 104 or other components of the cervical sizing device 300 obstructing the user's view of the arcuate contact pads 312, 314.

While the adjustable cervical sizing device 100 has been described as having arcuate contact pads 112, 114 positioned near distal end regions of the elongate arms 102, 104, pads or members of other shapes can alternatively be used. In certain implementations, for example, straight or linear members can be used in place of the arcuate contact pads 112, 114. Alternatively, members of various other shapes that permit substantially opposite outer surfaces of the cervix to be gently clamped therebetween in order to determine the approximate diameter of the cervix being measured can be used.

Figure 11:
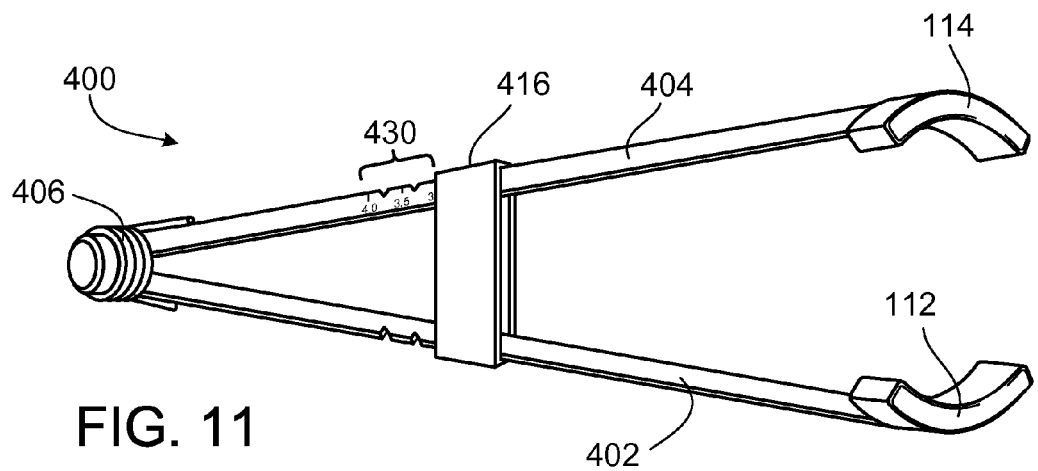
FIG. 11 is a front, perspective view of an adjustable cervical sizing device that includes pivotable arms that are biased away from one another by a torsion spring and a slidable locking member that can be used to fix the arms and arcuate members attached to distal end regions of the arms in several different positions relative to one another.

While the adjustable cervical sizing device described above has been described as including elongate arms 102, 104 that are pivotably connected to one another in their central regions by the pin 106, other arrangements are possible. Referring to FIG. 11, for example, an adjustable cervical sizing device 400 includes elongate arms 402, 404 that are pivotably connected to one another at their proximal ends by a torsion spring 406 that biases the arms 402, 404 away from one another. The cervical sizing device 400 further includes a slidable collar 416 that can be positioned at various different locations along the arms 402, 404 to hold the arms 402, 404 and the arcuate contact pads 112, 114 extending from distal end regions of the arms 402, 404 in different fixed positions relative to one another. The arm 404 includes a measurement scale 430 similar to the measurement scale 130 described above that can indicate to the user, based on the position of the collar 416 along the measurement scale 430, how far apart the arcuate contact pads 112, 114 are from one another. Based on this reading, the user can similarly determine the approximate size (e.g., the approximate diameter) of a patient's cervix when the arcuate contact pads 112, 114 are placed in contact with opposite sides of the outer surface of the patient's cervix.

Figure 12:
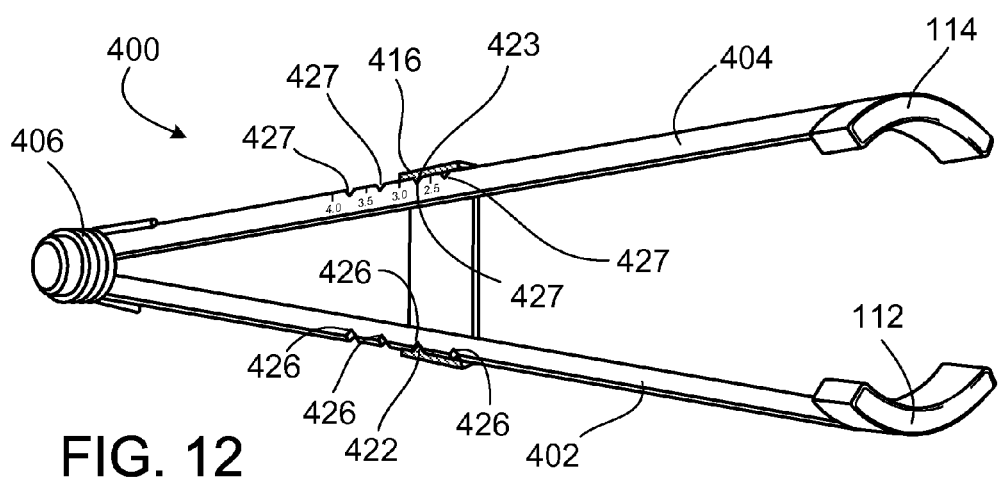
FIG. 12 is a front, perspective view of the adjustable cervical sizing device of FIG. 11 with the slidable locking member shown in a cut-away view to illustrate projections of the slidable locking member engaged in recesses formed in the pivotable arms to hold the arms and the arcuate members attached to the distal end regions of the arms in a fixed position relative to one another.

As shown in FIG. 12, which illustrates a cut-away view of the collar 416 of the cervical sizing device 400, projections 422, 423 extend from inner surfaces of the collar 416 that ride along outer surfaces of the arms 402, 404. Each of the arms 402, 404 forms a series of recesses 426, 427 that extend inwardly from those outer surfaces of the arms 402, 404. As the projections 422, 423 become engaged in the recesses 426, 427, the collar 416 is prevented from sliding along the arms 402, 404, which causes the arms 402, 404 and the arcuate contact pads 112, 144 that extend from the distal end regions of the arms 402, 404 to become fixed relative to one another. The proximal edge of the collar 416 will substantially align with one of the markings of the measurement scale 430 when the projections 422, 423 are disposed within associated recesses 426, 427 of the arms 402, 404 to indicate to the user the approximate distance between the arcuate contact pads 112, 114. In order to transition from one fixed position to another, the user can gently press the arms 402, 404 together and then slide the collar 416 from one engaged position (i.e., one position in which the projections 422, 423 are engaged in associated recesses 426, 427 of the arms) to a different engaged position.

Figure 13:
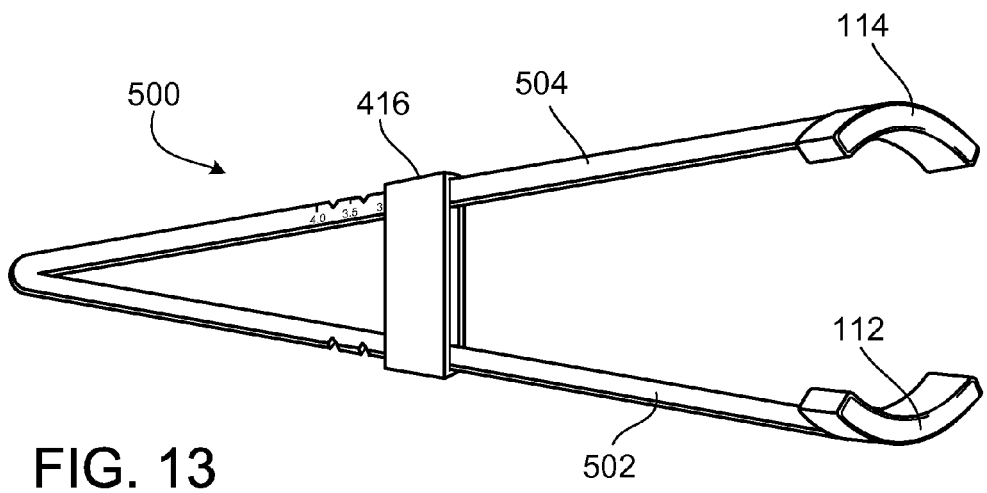
FIG. 13 is a front, perspective view of an adjustable cervical sizing device that includes pivotable arms that are integrally formed from a single piece of material and a slidable locking member that can be used to fix the arms and arcuate members attached to distal end regions of the arms in several different positions relative to one another.

While the cervical sizing device 400 of FIGS. 11 and 12 has been described as including elongate arms 402, 404 that are pivotably connected to one another by the torsion spring 406 positioned near the proximal ends of the elongate arms 402, 404, the cervical sizing device can alternatively be formed of a single piece of material (e.g., spring steel or plastic) that is bent into a U-shape to provide two elongate arms that are biased away from one another. As shown in FIG. 13, for example, an adjustable cervical sizing device 500 includes a single member of spring steel or plastic that has been bent into a U-shape to form two elongate arms 502, 504 that are biased away from one another. Each of the arms 502, 504 of the cervical sizing device 500 includes a series of recesses that extend inwardly from outer surfaces of the arms 502, 504 and engage the projections 422, 423 of the collar 416 to hold the arms 502, 504 and the arcuate contact pads 112, 114 in a fixed position relative to one another. The arm 504 also includes a measuring scale similar to the measuring scale 430 of the cervical sizing device 400 described above. Because the arms 502, 504 are formed from a single piece of material, the cost and complexity of manufacturing the cervical sizing device 500 can be reduced relative to certain other cervical sizing devices described herein.

While each of the arms of the cervical sizing device 400, 500 has been described as including a series of recesses and the collar 416 has been described as having projections 422, 423 that extend from opposite inner surfaces of the collar 416, in certain implementations, only one of the arms includes recesses and a projection extends only from the inner surface of the collar that rides along the arm that includes the recesses.

While the collar 416 has been illustrated as a hollow, rectangular member, it should be understood that collars of any of various different shapes that allow for locking of the arms of the cervical sizing devices 400, 500 in different positions without freely rotating about the arms can be used. As an example, an oval collar can alternatively be used.

Figure 14:
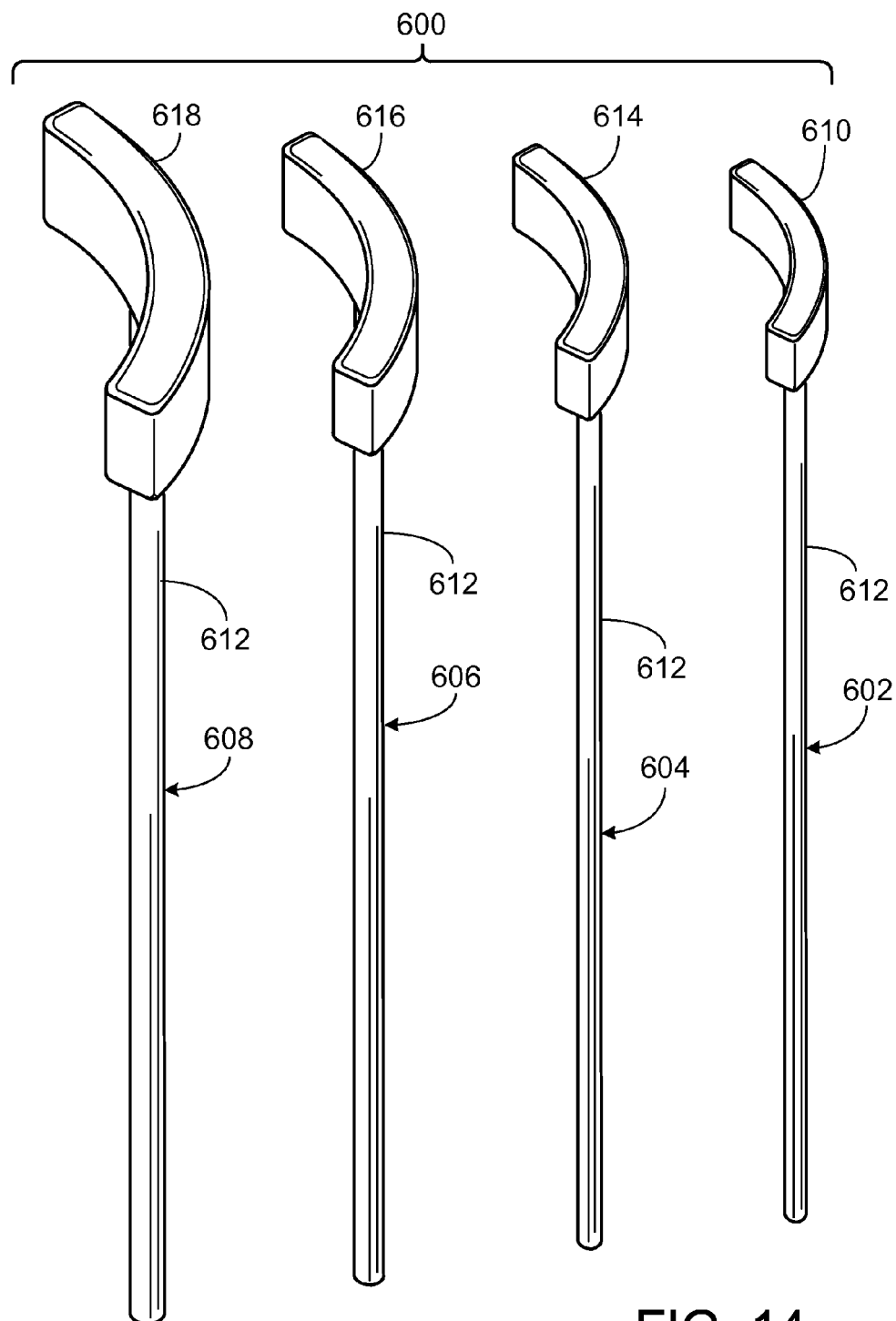
FIG. 14 illustrates a kit that includes multiple different non-adjustable cervical sizing devices, each of which includes a ring segment extending from a rod.

While the cervical sizing devices discussed above have been described as being adjustable, non-adjustable cervical sizing devices can alternatively be used. As shown in FIG. 14, for example, a kit 600 includes multiple different non-adjustable cervical sizing devices 602, 604, 606, 608. Referring first to the cervical sizing device 602, the cervical sizing device 602 includes a ring segment 610 extending from the distal end region of a rod 612. The ring segment 610 can, for example, be integrally formed with the rod 612 or can be attached to (e.g., welded to) the rod 612. The ring segment 610 has a radius of curvature of about 1.25 centimeters, which corresponds to the radius of curvature of the colpotomizer cup 132, which, as described above, has an inner diameter of about 2.5 centimeters. The cervical sizing device 602 can be formed of any of the various materials described above with respect to the cervical sizing device 100.

The cervical sizing devices 604, 606, 608 are generally the same as the cervical sizing device 602, but the ring segments 614, 616, 618 of the cervical sizing devices 604, 606, 608 have larger radii of curvature than the ring segment 610 of the cervical sizing device 602. In particular, the radii of curvature of the ring segments 614, 616, 618 are 1.5 centimeters, 1.75 centimeters, and 2.0 centimeters, respectively, which are substantially the same as the radii of curvature of the colpotomizer cups 134, 136, 138, which, as described above, have inner diameters of about 3.0 centimeters, 3.5 centimeters, and 4.0 centimeters, respectively. The length of the ring segments 610, 614, 616, and 618 can range from about 20 degrees to about 180 degrees.

In order to determine the approximate size of a patient's cervix using the cervical sizing devices 604, 606, 608, the user first grasps the proximal end region of the rod 612 of one of those devices and inserts the device into the patient's vagina. The cervical sizing device is advanced until the ring segment of the device is adjacent the outer surface of the cervix. The user then compares the radius of curvature of the ring segment of the cervical sizing device to the outer surface of the cervix to determine the approximate size (i.e., outer diameter) of the cervix. This procedure can be repeated with more than one (e.g., with all) of the cervical sizing devices 602, 604, 606, 608 if desired. The ring segment 610, 614, 616, 618 that most closely conforms to the outer shape of the cervix, as viewed by the user, can be used to approximate the outer diameter of the cervix. In other words, the cervix can be determined to have an approximate radius of curvature that equals the radius of curvature of the ring segment 610, 614, 616, 618 to which the outer surface most closely conforms. The approximate outer diameter of the cervix can then be easily determined by simply multiplying the approximated radius of curvature of the cervix by two. In certain implementations, each of the cervical sizing devices 602, 604, 606, 608 is labeled with the size of its corresponding colpotomizer cup.

While the ring segments 610, 614, 616, 618 of the cervical sizing devices 602, 604, 606, 608 have been described as being integrally formed with or permanently attached to the rod 612 of each of those devices, in certain implementations, the ring segments 610, 614, 616, 618 and the rods 612 are formed to permit a releasably coupling such that a single rod can be interchanged with multiple ring segments of differing curvature to form multiple different sized cervical sizing devices. Examples of suitable connection mechanisms for releasably coupling the rod to the different ring segments include bayonet-type clamping mechanisms, screw thread mechanisms, spring loaded ball/recess detent mechanisms, retractable sleeve with cam action ball in groove lock mechanisms, spring latch finger mechanisms, magnetic attachment mechanisms, and/or ¼ turn pin in groove attachment mechanisms.

Figure 15:
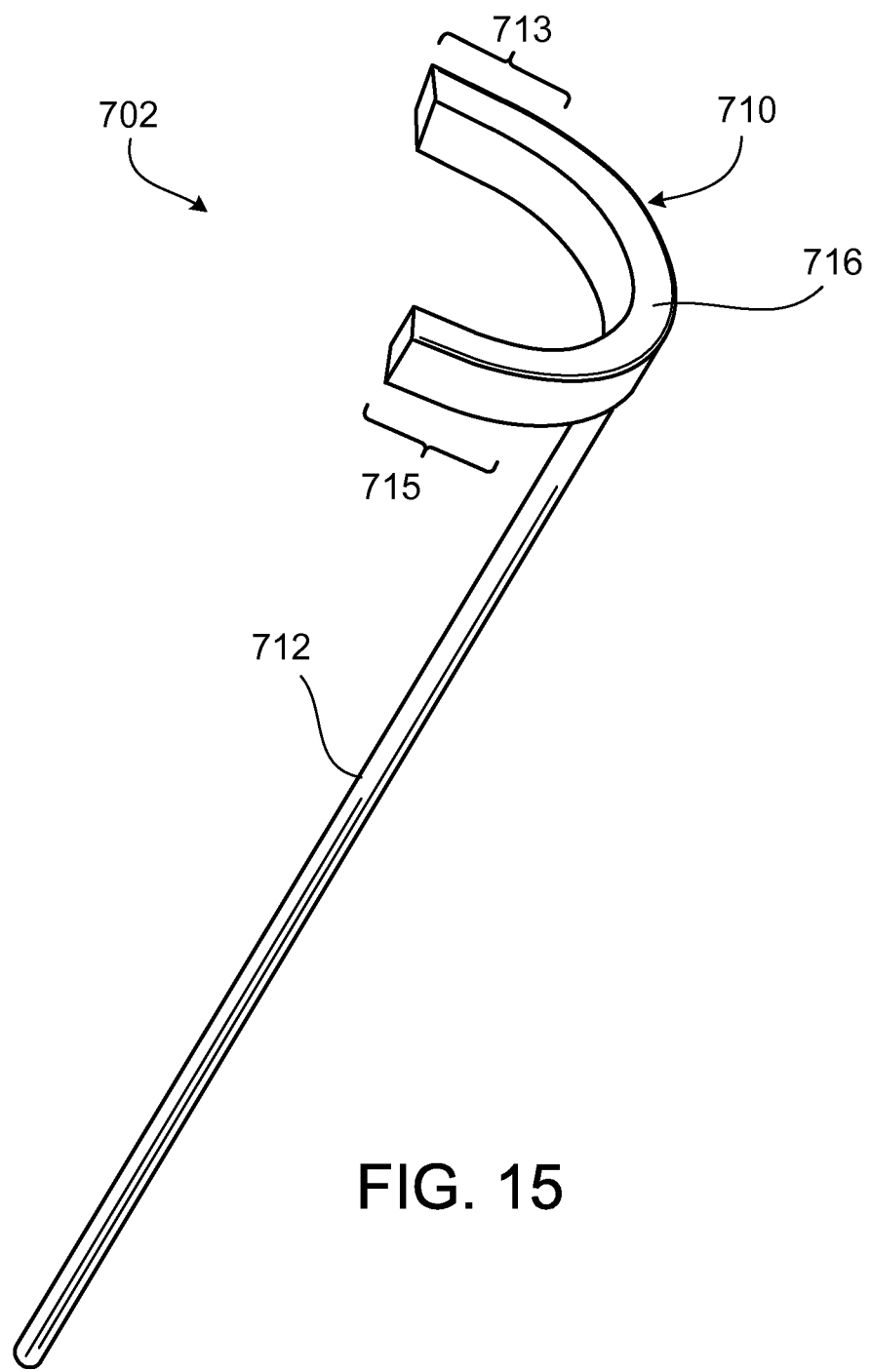
FIG. 15 illustrates a non-adjustable cervical sizing device that includes a cervix contact pad including straight segments that extend tangentially from the ends of a ring segment.

While each of the ring segments 610, 614, 616, and 618 has been illustrated as having a substantially constant radius of curvature, it should be understood that other type of cervix contact pads that include straight segments extending substantially tangentially from the free ends of a curved portion to form U-shaped members can be used. As shown in FIG. 15, for example, a non-adjustable cervical sizing device 702 include a U-shaped contact pad 710 attached to a distal end region of a rod 712. The U-shaped contact pad 710 is comprised of straight segments 713, 715 that extend substantially tangentially from opposite ends of a curved segment 716. Due to the straight segments 713, 715, the contact pad 710 extends further outward from the rod 712 and thus provides the user with a better view of the contact between the contact pad 710 and the patient's cervix during use.

Figure 16:
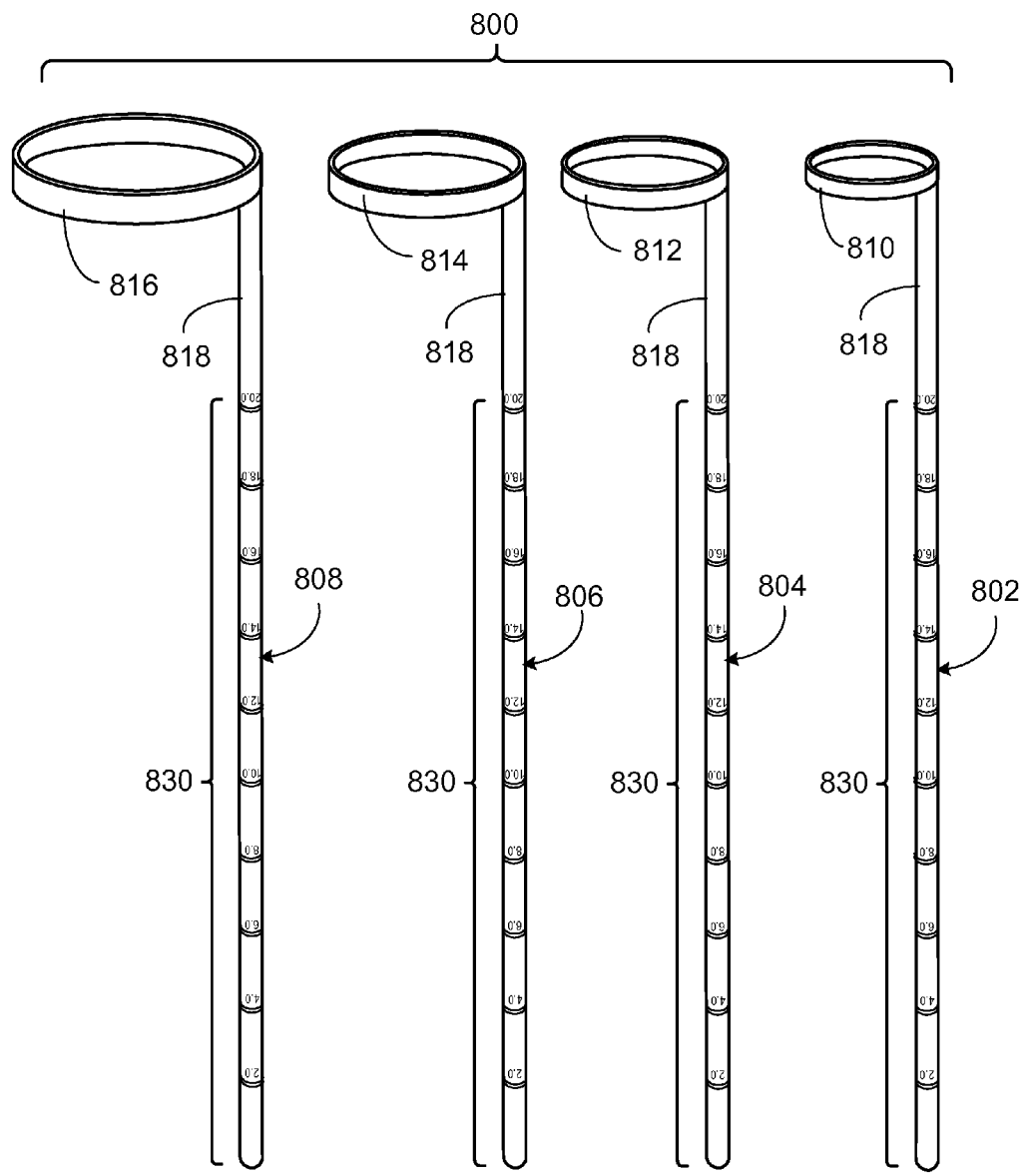
FIG. 16 illustrates a kit that includes multiple different non-adjustable cervical sizing devices, each of which includes a ring-shaped sizing member extending from a rod.

While the cervical sizing devices of FIGS. 14 and 15 have been described as including ring segments for determining an approximate size of a cervix, in certain implementations, a complete ring-shaped sizing member can be used. FIG. 16 illustrates a kit 800 that includes multiple different non-adjustable cervical sizing devices 802, 804, 806, 808 including ring-shaped sizing members 810, 812, 814, 816 attached to a rod 818. The ring-shaped sizing members 810, 812, 814, 816 have inner diameters that substantially match the inner diameters of the colpotomizer cups 132, 134, 136, 138 (shown in FIG. 5). In particular, the ring-shaped sizing members 810, 812, 814, 816 have inner diameters of about 2.5 centimeters, 3.0 centimeters, 3.5 centimeters, and 4.0 centimeters, respectively. The cervical sizing devices 802, 804, 806, 808 can be constructed in a manner similar to the cervical sizing devices 602, 604, 606, 608 described above. For example, the ring-shaped sizing members 810, 812, 814, 816 can be either permanently attached or releasably coupled to the rod 818 using techniques described above.

The cervical sizing devices 802, 804, 806, 808 are also used in substantially the same way as the cervical sizing devices 602, 604, 606, 608 described above. During use, the ring-shaped member of one of the cervical sizing devices 802, 804, 806, 808 is inserted into the vagina of a patient and positioned around the patient's cervix in much the same way as the ring segments 610, 614, 616, 618 discussed above. Due to the increased size of the ring-shaped sizing members 810, 812, 814, 816 compared to the ring segments 610, 614, 616, 618, it might be somewhat more difficult to position the ring-shaped members around the cervix in this way. However, due to the slenderness of the rod 818 to which each of the ring-shaped sizing members 810, 812, 814, 816 is attached and the relative slimness of the ring-shaped members themselves, it would be easier to navigate the ring into position around the patient's cervix than it would be to navigate a colpotomizer cup on the end of a uterine manipulator shaft into the same position, as is currently done in some cases to determine the approximate size of the cervix. In addition, the slenderness of the rod 418 and the slimness of the ring-shaped member allow the user to more easily view the ring-shaped member positioned around the cervix. As a result, the speed with which the measurement is made can be significantly reduced and the reliability with which the measurement is made can be significantly increased relative to certain conventional sizing techniques.

Still referring to FIG. 16, the proximal end region of the rod 818 of each cervical sizing device 802, 804, 806, 808 includes a uterus depth measurement scale 830. As shown, the uterus depth measurement scale 830 includes a series of ring-shaped depressions 832 that encircle the rod 818 and an engraved or printed numerical value associated with each of the ring-shaped depressions 832. On the illustrated device, the ring-shaped depressions 832 are provided in 2.0 centimeter increments such that the most proximal ring-shaped depression 832 is positioned approximately 2.0 centimeters from the proximal tip of the rod 818, the next most proximal ring-shaped depression 832 is positioned approximately 4.0 centimeters from the proximal tip of the rod 818, and so on. The most distal ring-shaped depression 832 in this case is positioned approximately 20.0 centimeters from the proximal tip of the rod 818.

To measure the approximate depth of a patient's uterus during a procedure, the cervical sizing device 802, 804, 806, 808 is turned upside down and the proximal end region of the rod 818 is passed through the patient's vagina and into the patient's uterus until the proximal tip of the rod 818 contacts the upper surface of the uterus. The user can then locate the ring-shaped depression 832 that is most closely aligned with the bottom surface of the uterus to determine the approximate depth of the patient's uterus. In particular, the approximate depth of the patient's uterus will be equal to the numerical marking (e.g., 8.0 centimeters, 10.0 centimeters, etc.) associated with that ring-shaped depression 832. In certain cases, the user is able to view the measurement scale 830 when the rod 818 is disposed within the patient's uterus in order to determine the approximate depth of the patient's uterus. Alternatively, the user can place his or her finger tip on the ring-shaped depression 832 determined by feel to be positioned nearest the bottom surface of the uterus and, while holding his or her finger tip in that position, can remove the rod 818 from the patient to see the numerical value (e.g., 8.0 centimeters, 10.0 centimeters, etc.) associated with that ring-shaped depression. The determined approximate depth of the patient's uterus can be useful for selecting and/or configuring certain components (e.g., uterine manipulator components) to be used during a subsequent procedure (e.g., a total laparoscopic hysterectomy (TLH) surgery) performed on the patient.

While the measurement scale 830 has been described as including ring-shaped depressions 832, other types of markings can alternatively or additionally be used. In certain implementations, for example, raised rings extend from the rod. Painted or printed rings can alternatively or additionally be used. Also, while the uterus depth measurement scales have all been described as including rings, it should be understood that lines and other markings that do not extend around the entire circumference of the rod can be used.

In addition, while the measurement scale 830 has been described as including numerical markings ranging from 2.0 centimeters to 20.0 centimeters and increasing by 2.0 centimeter increments, it should be understood that the uterus depth measurement scales can include any of various other marking schemes. In certain implementations, for example, the markings of the uterus depth measurement scale are provided in 1.0 centimeter increments. In other implementations, for example, the markings of the uterus depth measurement scale are provided in 0.5 centimeter increments.

In addition, it should be understood that any of the various uterus depth measurement scales described above can be provided on the rods 612, 712 of the cervical sizing devices 602, 604, 606, 608, and 702 to enable those devices to be used to determine the approximate depth of a patient's uterus.

While the kits 600, 800 have been described as including only multiple cervical sizing devices, it should be understood that such kits can also include multiple colpotomizer cups of different sizes.

While the methods described above relate to the selection of an appropriate sized colpotomizer cup, the methods can be used to select any of various other types of gynecological instruments that are designed to be used with cervixes of certain sizes or certain size ranges. For example, the determination of the approximate size of a patient's cervix using the methods described above can be used to assist a physician in selecting a pessary that is most suitable for use in a patient undergoing a pelvic support procedure.

The methods and devices described herein can also be used for various obstetrical purposes. For example, the cervical sizing devices and methods can be used to assist in diagnosing cervical incompetence.

Other implementations are within the scope of the following claims.

What is claimed is:

1. A cervical sizing device in combination with a plurality of colpotomizer cups, the cervical sizing device comprising:
   first and second elongate arms that are pivotable about a pivot point relative to one another;
   first and second cervix contact members positioned at distal end regions of the first and second elongate arms, respectively, such that the first and second cervix contact members can be moved toward or away from one another as the elongate arms are pivoted about the pivot point relative to one another, the first and second cervix contact members being arcuate members that are sized to conform to an outer surface of a cervix; and
   a measurement device positioned in a proximal portion of the cervical sizing device, wherein the measurement device indicates a size of the cervix when the cervix contact members are brought into contact with opposed outer surface regions of the cervix, wherein the measurement device comprises a measurement scale thereon that a user can use to determine the size of the cervix, and wherein the measurement scale comprises only values that correspond to the plurality of colpotomizer cups.

2. The combination of claim 1, wherein the measurement device comprises first and second members that extend from the first and second elongate arms, respectively, and are configured to overlap one another as the first and second elongate arms are pivoted about the pivot point.

3. The combination of claim 2, wherein at least one of the members of the measurement device comprises the measurement scale that can be used to determine the size of the cervix when the cervix contact members are brought into contact with the opposing outer surface regions of the cervix.

4. The combination of claim 3, wherein the measurement device comprises a series of detents that allow the first and second members of the measurement device to be releasably fixed relative to one another in a plurality of different positions.

5. The combination of claim 4, wherein the detents comprise a projection that extends from one of the members of the measurement device and a plurality of recesses formed in the other member of the measurement device, each of the recesses sized to receive at least a portion the projection therein.

6. The combination of claim 4, wherein the measurement device is configured to provide tactile feedback to a user of the cervical sizing device when the measurement device is moved into anyone of the plurality of different positions.

7. The combination of claim 3, wherein the measurement scale indicates a distance between the cervix contact members.

8. The combination of claim 3, wherein the measurement scale is printed on or engraved in one of the members of the measurement device.

9. The combination of claim 1, wherein the measurement device is configured to releasably fix the cervical sizing device in a plurality of different positions such that the cervix contact members can be releasably fixed at a plurality of different distances of separation relative to one another.

10. The combination of claim 9, wherein the measurement device is configured to provide tactile feedback to a user of the cervical sizing device when the cervical sizing device is moved into one of the plurality of different positions from another of the plurality of different positions.

11. The combination of claim 1, wherein the cervical sizing device is configured such that the measurement device remains outside of a patient when the cervix contact members are positioned around a cervix of the patient.

12. The combination of claim 1, wherein the cervical sizing device comprises first and second graspable loops extending from the first and second elongate arms, respectively, in a proximal end region of the cervical device.

13. A kit, comprising:
   a plurality of colpotomizer cups that are configured to receive a cervix; and
   a cervical sizing device, comprising
      first and second elongate arms that are pivotable about a pivot point relative to one another;
      first and second cervix contact members positioned at distal end regions of the first and second elongate arms, respectively, such that the first and second cervix contact members can be moved toward or away from one another as the elongate arms are pivoted about the pivot point relative to one another, the first and second cervix contact members being arcuate members that are sized to conform to an outer surface of a cervix; and
      a measurement device positioned in a proximal portion of the cervical sizing device, wherein the measurement device indicates a size of the cervix when the cervix contact members are brought into contact with opposed outer surface regions of the cervix.

14. The kit of claim 13, wherein each of the colpotomizer cups defines a cavity for receiving a cervix.

* * * * *

UNITED STATES PATENT AND TRADEMARK OFFICE
CERTIFICATE OF CORRECTION

| | | Page 1 of 1 |
|---|---|---|
| PATENT NO. | : 8,876,736 B2 | |
| APPLICATION NO. | : 13/860200 | |
| DATED | : November 4, 2014 | |
| INVENTOR(S) | : Charles Sherts et al. | |

It is certified that error appears in the above-identified patent and that said Letters Patent is hereby corrected as shown below:

In the Claims,

<u>Column 18</u>
Line 2, in Claim 5, after "portion" insert -- of --

Signed and Sealed this
Seventeenth Day of February, 2015

Michelle K. Lee
*Deputy Director of the United States Patent and Trademark Office*